US008835092B2

(12) United States Patent
Watanabe et al.

(10) Patent No.: US 8,835,092 B2
(45) Date of Patent: Sep. 16, 2014

(54) RESIST UNDERLAYER FILM COMPOSITION, PROCESS FOR FORMING RESIST UNDERLAYER FILM, PATTERNING PROCESS AND FULLERENE DERIVATIVE

(75) Inventors: Takeru Watanabe, Jyoetsu (JP); Takeshi Kinsho, Jyoetsu (JP); Tsutomu Ogihara, Jyoetsu (JP); Katsuya Takemura, Jyoetsu (JP); Toshihiko Fujii, Jyoetsu (JP); Daisuke Kori, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 260 days.

(21) Appl. No.: 13/015,094

(22) Filed: Jan. 27, 2011

(65) Prior Publication Data

US 2011/0195362 A1   Aug. 11, 2011

(30) Foreign Application Priority Data

Feb. 5, 2010   (JP) ................................ 2010-024379

(51) Int. Cl.
*G03F 7/095* (2006.01)
*G03F 7/11* (2006.01)
*G03F 7/40* (2006.01)
*G03F 7/09* (2006.01)
*C07C 69/753* (2006.01)
*C08L 61/06* (2006.01)

(52) U.S. Cl.
CPC .............. *C07C 69/753* (2013.01); *G03F 7/094* (2013.01); *C08L 61/06* (2013.01); *G03F 7/40* (2013.01); *C07C 2104/00* (2013.01)
USPC .................... 430/270.1; 430/271.1; 430/313; 430/316

(58) Field of Classification Search
USPC ............................. 430/270.1, 271.1, 313, 316
See application file for complete search history.

(56) References Cited

U.S. PATENT DOCUMENTS

| 5,739,376 | A * | 4/1998 | Bingel .............................. 560/51 |
| 7,476,486 | B2 * | 1/2009 | Hatakeyama et al. ..... 430/270.1 |
| 2002/0106909 | A1 | 8/2002 | Kato et al. |
| 2008/0118874 | A1 * | 5/2008 | Robinson et al. .............. 430/327 |
| 2008/0279231 | A1 * | 11/2008 | Farber et al. ..................... 372/21 |
| 2010/0035181 | A1 * | 2/2010 | Sakaguchi et al. ......... 430/271.1 |
| 2010/0081082 | A1 | 4/2010 | Yoshimura et al. |

FOREIGN PATENT DOCUMENTS

| JP | A-06-061138 | 3/1994 |
| JP | A-2002-334869 | 11/2002 |
| JP | A-2004-205685 | 7/2004 |
| JP | 2004-256754 | * 9/2004 |
| JP | A-2004-264710 | 9/2004 |
| JP | A-2005-331918 | 12/2005 |
| JP | A-2006-227391 | 8/2006 |
| JP | A-2007-199653 | 8/2007 |
| JP | A-2008-164806 | 7/2008 |
| JP | A-2009-269953 | 11/2009 |
| WO | WO 2004/066377 A1 | 8/2004 |
| WO | WO 2008/062888 A1 | 5/2008 |
| WO | WO 2008/126804 | * 10/2008 |
| WO | WO 2008/126804 A1 | 10/2008 |

OTHER PUBLICATIONS

"Dow Epoxy Novolac Resins", published by the Dow Chemical Company in Oct. 1998.*
Machine translation of JP 2004-256754, published on Sep. 16, 2004.*
Ya-Ping Sun, Glenn E. Lawson, Jason E. Riggs, Bin Ma, Naixing Wang, and Dwella Motton—Photophysical and Nonlinear Optical Properties of (60)Fullerene Derivatives, J. Phys. Chem. A 1998, 102, 5520-5528.*
Apr. 17, 2012 Japanese Office Action issued in Japanese Patent Application No. 2010-024379 (with partial translation).
Troshin et al., "Material Solubility-Photovoltaic Performance Relationship in the Design of Novel Fullerene Derivatives for Bulk Heterojunction Solar Cells," *Advanced Functional Materials*, vol. 19, pp. 779-788, 2009.
Hirsch et al., "Fullerene Chemistry in Three Dimensions: Isolation of Seven Regioisomeric Bisadducts and Chiral Trisadducts of $C_{60}$ and Di(ethoxy-carbonyl)methylene," *Angew. Chem. Int. Ed. Engl.*, vol. 33, No. 4, pp. 437-438, 1994.
Lamparth et al., "Reversible Template-Directed Activation of Equatorial Double Bonds of the Fullerene Framework: Regioselective Direct Synthesis, Crystal Structure, and Aromatic Properties of $T_h$-$C_{66}(COOEt)_{12}$," *Angew. Chem. Int, Ed. Engl.*, vol. 34, No. 15, pp. 1607-1609, 1995.
Nierengarten et al., "Regio- and Diastereoselective Bisfunctionalization of $C_{60}$ and Enantioselective Synthesis of a $C_{60}$ Derivative with a Chiral Addition Pattern," *Angew. Chem. Int. Ed. Engl.*, vol. 35, No. 18, pp. 2101-2103, 1996.
Bingel, Carsten, "Cyclopropanierung von Fullerenen," *Chem. Ber.*, vol. 126, pp. 1957-1959, 1993.
Camps et al "The $C_{60}$ Core: A Versatile Tecton for Dendrimer Chemistry," *Chem. Eur. J.*, vol. 3, No. 4, pp. 561-567, 1997.
Li et al., "Novel Copolyamides Containing [60]Fullerene in the Main Chain," *Chemistry Letters*, vol. 1997, pp. 1037-1038, 1997.
Isaacs et al., "Improved Purification of $C_a$ and Formation of σ- and π-Homoeromatic Methano-Bridged Fullerenes by Reaction with Alkyl Diazoacetates," *Helvetica Chimica Acta*, vol. 76, pp. 1231-1250, Nov. 15, 1993.

(Continued)

*Primary Examiner* — Anca Eoff
(74) *Attorney, Agent, or Firm* — Oliff PLC

(57) ABSTRACT

There is disclosed a resist underlayer film composition of a multilayer resist film used in lithography including (A) a fullerene derivative having a carboxyl group protected by a thermally labile group and (B) an organic solvent. There can be a resist underlayer film composition of a multilayer resist film used in lithography for forming a resist underlayer in which generation of wiggling in substrate etching can be highly suppressed and the poisoning problem in forming an upper layer pattern using a chemically amplified resist can be avoided, a process for forming the resist underlayer film, a patterning process and a fullerene derivative.

13 Claims, 1 Drawing Sheet

(56) References Cited

OTHER PUBLICATIONS

Bondon at al., "Electrochemistry of Mono-through Hexakis-adducts of $C_{60}$," *Helvetica Chimica Acta*, vol. 78, pp. 1334-1344, Jun. 9, 1995.

Herrmann et al., "Multiple Cyclopropanations of $C_{70}$: Synthesis and Characterization of Bis-, Tris-, and Tetrakis-adducts and Chiroptical Properties of Bis-adducts with Chiral Addends, Including a Recommendation for the Configurational Description of Fullerene Derivatives with a Chiral Addition Pattern," *Helvetica Chimica Acta*, vol. 78, pp. 1673-1704, Jul. 31, 1995.

Chuard at al., "First Fullerene[60]-Containing Thermotropic Liquid Crystal," *Helvetica Chimica Acta*, vol. 79, pp. 736-741, Jan. 9, 1996.

Herrmann et al., "Synthesis, Separation, and Characterization of Optically Pure $C_{76}$ Mono-Adducts," *Helvetica Chimica Acta*, vol. 79, pp. 1741-1756, Jul. 16, 1996.

Hirsch et al., "Regiochemistry of Multiple Additions to the Fullerene Core: Synthesis of a $T_h$-Symmetric Hexakisadduct of $C_{60}$ with Bis(ethoxycarbonyl)methylene," *J. Am. Chem. Soc.*, vol. 116, No. 20, pp. 9385-9386, 1994.

Camps et al., "Efficient cyclopropanation of $C_{60}$ starting from malonates," *J. Chem. Soc., Perkin Trans.*, vol. 1, pp. 1595-1596, 1997.

Bingel et al., "Biscyclopropanation of $C_{70}$," *Liebigs Ann*, vol. 1995, pp. 1551-1553, 1995.

Seino et al., "Sub-45nm Resist Process Using Stacked-Mask Process," *Proc. of SPIE*, vol. 6923, pp. 69232O-1-69232O-8, 2008.

Abe et al., "Sub-55-nm Etch Process Using Stacked-Mask Process," *2005 Dry Process International Symposium*, pp. 11-12, 2005.

Greene et al., "Protective Groups in Organic Synthesis, Third Edition," pp. 373-378, 1999.

Johnson, Donald W., "Thermolysis of Positive Photoresists," *SPIE—Advances in Resist Technology*, vol. 469, pp. 72-79, 1984.

Wilson et al., "2,6-Dimethoxyanthracene—A Directing Group for Regioselective Bisaddition to $C_{60}$," *Tetrahedron Letters*, vol. 36, No. 32, pp. 5707-5710, 1995.

Wang et al., "A Superior Synthesis of [6,6]-Methanofullerenes: The Reaction of Sulfonium Ylides with $C_{60}$," *Tetrahedron Letters*, vol. 36, No. 38, pp. 6843-6846, 1995.

Brettreich et al., "A Highly Water-Soluble Dendro[60]fullerene," *Tetrahedron Letters*, vol. 39, pp. 2731-2734, 1998.

Nierengarten et al., "Regioselective Bisaddition to $C_{60}$ with Bis(β-Keto Esters)," *Tetrahedron Letters*, vol. 39, pp. 2747-2750, 1998.

\* cited by examiner

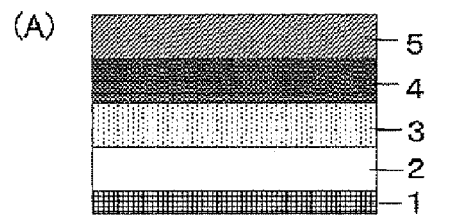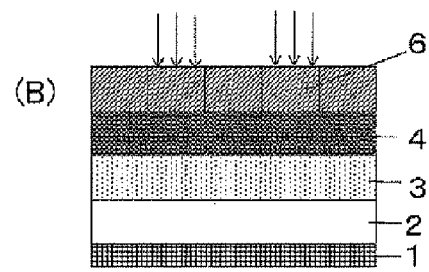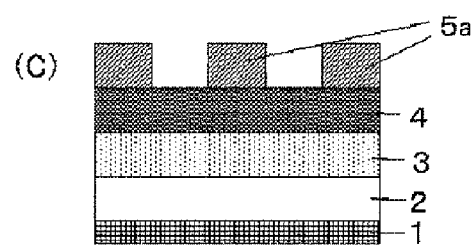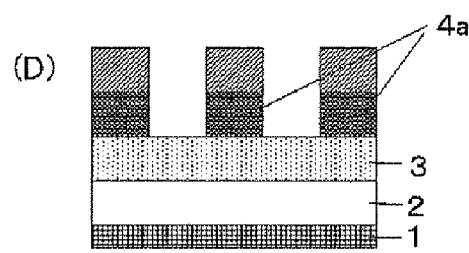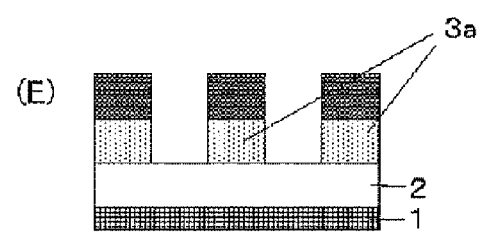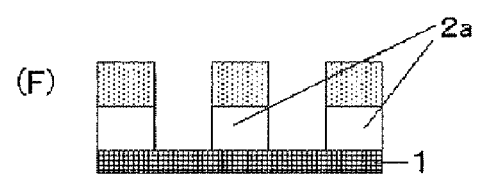

RESIST UNDERLAYER FILM COMPOSITION, PROCESS FOR FORMING RESIST UNDERLAYER FILM, PATTERNING PROCESS AND FULLERENE DERIVATIVE

BACKGROUND OF THE INVENTION

1. Field of the Invention

The present invention relates to a resist underlayer film composition effective for a multilayer resist process used for microfabrication in a process for manufacturing semiconductor devices and the like, a process for forming a resist underlayer film using the same, a resist patterning process using the underlayer film composition suitable for exposure by deep ultraviolet ray, KrF excimer laser light (248 nm), ArF excimer laser light (193 nm), $F_2$ laser light (157 nm), $Kr_2$ laser light (146 nm), $Ar_2$ laser light (126 nm), soft X ray (EUV), an electron beam (EB), an ion beam, X ray and the like, and a fullerene derivative useful in these technical fields.

2. Description of the Related Art

As higher integration and higher speed of LSI are realized, finer pattern size is achieved rapidly. Along with the achievement of finer pattern size, the lithography techniques have accomplished micropatterning by using light sources with shorter wavelength and properly selecting resist compositions corresponding to the light sources. As for such compositions, positive photoresist compositions used as a monolayer are mainly selected. Each of these monolayer positive photoresist compositions has a skeleton providing an etching resistance against dry etching with chlorine-based gas plasma or fluorine-based gas plasma in the resist resin, and has resist mechanism that an exposed area turns soluble, thereby forming a pattern by dissolving the exposed area and dry etching a substrate to be processed to which the resist composition is applied by using the remained resist pattern as an etching mask.

However, when a pattern is rendered finer, that is, a pattern width is rendered narrower, without changing the thickness of a photoresist film to be used, resolution performance of the photoresist film is deteriorated. In addition, developing the pattern of the photoresist film with a developer causes a pattern collapse because a so-called aspect ratio of the pattern becomes too high. Therefore, the thickness of a photoresist film has been made thinner along with achieving a finer pattern.

On the other hand, for processing a substrate to be processed, a method to process the substrate by dry etching by using a pattern-formed photoresist film as an etching mask is usually used. Actually however, there is no dry etching method capable of providing an absolute selectivity between the photoresist film and the substrate to be processed. Therefore, the resist film is also damaged and collapsed during processing the substrate, so that the resist pattern cannot be transferred to the substrate to be processed correctly. Accordingly, as a pattern becomes finer, it has been required that a resist composition has a higher dry etching resistance.

In addition, the use of shorter wavelength exposure radiations has required resins used for photoresist compositions to have low absorbance at the wavelength to be used. Accordingly, as the radiation shifts from i-line to KrF and to ArF, the resin shifts from novolac resins to polyhydroxystyrene, and to resins having an aliphatic polycyclic skeleton. Along with this shift, an etching rate of the resin actually becomes higher under the dry etching conditions mentioned above, and recent photoresist compositions having a high resolution tend to have a low etching resistance.

As a result, a substrate to be processed has to be dry etched with a thinner photoresist film having lower etching resistance. The need to provide a material for this process and the process itself has become urgent.

A multilayer resist process is one of solutions for these problems. This method is as follows: an intermediate film having a different etching selectivity from a photoresist film, that is, a resist upper layer film, is set between the resist upper layer film and a substrate to be processed to obtain a pattern in the resist upper layer film; the pattern is transferred to the intermediate film by dry etching by using the upper layer resist pattern as a dry etching mask; and then the pattern is transferred to the substrate to be processed by dry etching by using the intermediate film as a dry etching mask.

In one example of a two-layer resist process, which is one of the multilayer resist processes, a silicon-containing resin is used for the upper layer resist composition and an organic resin having a high carbon content such as a novolac resin is used for the underlayer film. The silicon resin has a good etching resistance to a reactive dry etching using oxygen plasma, while it is easily removed by etching using fluorine-based gas plasma. On the other hand, the novolac resin is easily removed by a reactive dry etching using oxygen plasma, while it has a good etching resistance to dry etching using fluorine-based plasma or chlorine-based gas plasma. In this example, a novolac resin film as a resist intermediate film is formed on a substrate to be processed and a resist upper layer film using a silicon-containing resin is formed on the resist intermediate film. Then, a pattern is formed in the silicon-containing resist film by irradiation of an energy beam and sequential aftertreatment such as development; part of the novolac resin, on which the resist pattern is removed, is removed by a reactive dry etching using oxygen plasma by using the pattern-formed silicon-containing resist film as a dry etching mask to transfer the pattern to the novolac film; and thereafter, the pattern can be transferred to the substrate to be processed by etching using fluorine-based plasma or chlorine-based gas plasma by using the pattern transferred to the novolac film as a dry etching mask.

In such a pattern transfer by the dry etching, when the etching resistance of the etching mask is sufficient, the transferred pattern having a relatively good profile is obtained. Thus, a problem such as a pattern collapse caused by friction and the like by a developer upon resist development hardly occurs, and a pattern having a relatively high aspect ratio can be obtained. Therefore, for example, when the resist film using the novolac resin has the thickness corresponding to the film thickness of the intermediate film, even in the fine pattern which could not be formed directly because of the pattern collapse upon development due to the aspect ratio, according to the above two-layer resist process, the novolac resin pattern having the sufficient thickness as the dry etching mask for the substrate to be processed is obtained.

The multi-layer resist process further include a three-layer resist process which can be performed by using a typical resist composition used in a monolayer resist process. For example, this method is configured to form: an organic film based on novolac or the like as a resist under layer film on a substrate to be processed; a silicon-containing film as a resist intermediate film thereon; and a usual organic photoresist film as a resist upper layer film thereon. Since the organic resist upper layer film exhibits an excellent etching selectivity ratio relative to the silicon-containing resist intermediate film for dry etching by fluorine-based gas plasma, the resist pattern is transferred to the silicon-containing resist intermediate film by means of dry etching based on fluorine-based gas plasma. According to this process, as well as two-layer resist process, patterns of novolac films having sufficient dry etching resistances for processing can be obtained insofar as patterns can be transferred to silicon-containing films, even by adopting: a resist composition which is difficult to be formed with a pattern having a sufficient film thickness for direct processing of a substrate to be processed; and a resist composition having an insufficient dry etching resistance for processing of a substrate.

While numerous techniques have been known (such as Japanese Patent Laid-Open (kokai) No. 2004-205685 and the like) for the organic underlayer film as described above, decrease of processing line width has been accompanied by such problems that phenomena of wiggling, bending, and the like of a resist underlayer film are caused when the resist underlayer film is used as a mask for etching a substrate to be processed (Proc. of Symp. Dry. Process, (2005), p 11), and these problems are caused notedly especially when a finer pattern of 40 nm or less is formed. Such wiggling of a finer pattern is considered to be caused by swell of the underlayer film due to an increased volume thereof and a lowered glass transition point thereof by a phenomenon having been reported, in which hydrogen atoms of a resist underlayer film are substituted with fluorine atoms during etching of a substrate by a fluorocarbon-based gas (Proc. Of SPIE Vol. 6923, 69232O, (2008)). In turn, it has been reported that the problem of wiggling can be prevented by adopting an organic material, which is low in hydrogen atom content ratio, as a resist underlayer film. In this respect, amorphous carbon films formed by CVD are each allowed to be extremely less in the number of hydrogen atoms in the film itself, and are effective for prevention of wiggling. However, CVD is unfortunately insufficient in filling-up characteristic of a stepped substrate, and it is often difficult to introduce a CVD apparatus due to the problems of its high cost and an increased footprint occupation area of the apparatus. Therefore, it will be able to obtain a remarkable merit of cost reduction by simplification of a process and an apparatus, if the above problem of wiggling is solved based on a resist underlayer film composition which can be formed into a film by coating, particularly by spin coating.

As the above-described film-forming material which is low in hydrogen atom content ratio and which can be coated and formed into a film, films each containing a fullerene derivative having extremely high in carbon ratio have been proposed. For example, a method for forming a film by fullerene itself (here, fullerene is a collective term of allotropes of carbon possessing a closed shell cluster composed of many carbon atoms, is typified by $C_{60}$ and $C_{70}$ and includes $C_{74}$, $C_{76}$, $C_{78}$, $C_{82}$, $C_{84}$, $C_{90}$, $C_{94}$, $C_{96}$, $C_{108}$ and further higher carbon clusters) was proposed at the earliest stage (Japanese Patent Laid-Open (kokai) No. H06-61138), but it was difficult to use fullerene itself because fullerene was extremely poor in solubility in a general solvent coated on a substrate. Accordingly, in Japanese Patent Laid-Open (kokai) No. 2004-264710, Japanese Patent Laid-Open (kokai) No. 2006-227391), for example, fullerene was converted to its derivative soluble in a solvent for application and the fullerene derivative was dispersed into an organic resin to obtain a cured film. However, because of the conversion of a fullerene to its derivative, a problem that the key hydrogen atom containing ratio largely increases has been caused. To solve that problem, in WO2008/62888, it was proposed to use a fullerene-amine adduct (aminated fullerene), which is a derivative having a possibility of generating a fullerene or a substance having a similar hydrogen atom containing ratio to a fullerene by heat decomposition. This technique is important in respect of maximizing the merit of using the fullerene derivative. On the other hand, in a multilayer resist process, an intermediate layer is formed on an underlayer film as appropriate, and then an upper layer resist is formed to form a pattern, while a chemically amplified resist acting by acid catalyst reaction is used as the upper layer resist. Therefore, when an amine base generated by heat decomposition of the fullerene derivative (fullerene-amine adduct) reaches the upper resist film even in minute amounts, it affects the acid catalyst reaction in forming the upper resist pattern to cause a so-called poisoning problem such as deterioration of a pattern profile and a development defect.

SUMMARY OF THE INVENTION

The present invention was made in view of the situation as mentioned above and has an object to provide a resist underlayer film composition of a multilayer resist film used in lithography for forming a resist underlayer in which generation of wiggling in substrate etching can be highly suppressed and the poisoning problem in forming an upper layer pattern using a chemically amplified resist can be avoided, a process for forming the resist underlayer film, a patterning process and a fullerene derivative.

In order to solve the above problems, the present invention provides a resist underlayer film composition of a multilayer resist film used in lithography including (A) a fullerene derivative having a carboxyl group protected by a thermally labile group and (B) an organic solvent.

Such a resist underlayer film composition enables that the fullerene derivative (A) is soluble in an organic solvent for application and part of a derivatization side chain which is necessary for dissolution in the organic solvent (thermally labile group) is thermally decomposed, thereby enabling to reduce a substantial hydrogen concentration of the underlayer film and to highly suppress generation of wiggling in etching. In addition, due to the structure of the fullerene derivative (A), a substance generated by the decomposition of the thermally labile group is not a basic compound such as amine, thereby enabling to suppress adverse effects on a pattern profile in patterning of the upper resist.

Further, it is preferable that the fullerene derivative has n partial structures represented by the following general formula (1).

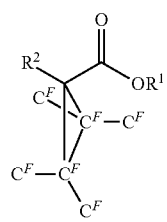

(1)

(In the formula, $R^1$ represents a thermally labile group; $R^2$ represents a hydrogen atom, a cyano group, $-COOR^3$, a linear, branched or cyclic alkyl group having 1 to 10 carbon atoms, an aryl group having 6 to 16 carbon atoms, a heteroaryl group having 4 to 16 carbon atoms or an aralkyl group having 7 to 20 carbon atoms, optionally containing a carbonyl group, an ether group, an ester group, a cyano group, a carboxyl group or a hydroxyl group; $R^3$ represents a hydrogen atom, $R^1$ or a linear, branched or cyclic alkyl group having 1 to 10 carbon atoms; $C^F$ represents a carbon atom constituting a fullerene skeleton of the fullerene derivative; and n represents an integer of 1 to 30.)

As above, as a preferable embodiment of the fullerene derivative (A), one having n partial structures represented by the foregoing general formula (1) is enumerated. In the foregoing general formula (1), the presence of $R^1$ is effective to secure a solubility of the fullerene derivative to the solvent for the underlayer film, and has a function to reduce the substantial hydrogen concentration of the underlayer film by being decomposed and removed in formation of the underlayer film and a heat treatment. In addition, due to the structure of $R^1$, a substance generated by the decomposition of $R^1$ is not a basic compound such as amine, thereby enabling to suppress adverse effects on a pattern profile in patterning of the upper resist.

Further, it is preferable that the fullerene derivative has n partial structures represented by the following general formula (1a).

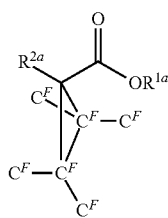

(1a)

(In the formula, $R^{1a}$ represents a substituted or an unsubstituted linear or cyclic tertiary alkyl group having 4 to 30 carbon atoms, optionally containing an unsaturated bond or an aromatic ring; $R^{2a}$ represents a hydrogen atom, a cyano group, —$COOR^{3a}$, a methyl group, an ethyl group, an acetyl group, a phenyl group, a naphthyl group, a furyl group, a benzoyl group or a naphthoyl group; $R^{3a}$ represents a hydrogen atom, $R^{1a}$ or a linear, branched or cyclic alkyl group having 1 to 14 carbon atoms; $C^F$ represents a carbon atom constituting a fullerene skeleton of the fullerene derivative; and n represents an integer of 1 to 30.)

As above, as a further preferable embodiment of the fullerene derivative (A), one having n partial structures represented by the foregoing general formula (1a) is enumerated.

That is, as a preferable thermally labile group in the fullerene derivative (A), a tertiary alkyl group is enumerated.

Further, it is preferable that the resist underlayer film composition includes a mixture of two or more kinds of the fullerene derivatives having a different n value from each other and the n value of the fullerene derivative having the highest presence ratio is an integer of 3 to 10.

As above, in view of a solubility in the organic solvent and film formability, it is preferable that the resist underlayer film composition includes a mixture of two or more kinds of the fullerene derivatives having a different n value from each other, and in this case, it is preferable that the n value of the fullerene derivative having the highest presence ratio is an integer of 3 to 10.

Further, it is preferable that the resist underlayer film composition further includes (C) a resin containing an aromatic ring.

As above, the resist underlayer film composition preferably further includes (C) a resin containing an aromatic ring, because film formability in spin coating, a filling-up characteristic of a stepped substrate and an etching resistance can be improved.

Further, the resist underlayer film composition can further include at least one or more kinds among (D) a compound containing a phenolic hydroxyl group, (E) an acid generator, (F) a crosslinker and (G) a surfactant.

As above, into the resist underlayer film composition of the present invention, (D) a compound containing a phenolic hydroxyl group, (E) an acid generator and (F) a crosslinker can be added for further promoting a cross-linking reaction and (G) a surfactant can also be added for improving coatability in spin coating.

Further, it is preferable that above-mentioned (C) a resin containing an aromatic ring contains at least, a compound (C1) obtained by a polycondensation reaction between a compound represented by the following general formula (2) and a compound represented by the following general formula (3) under an acid condition.

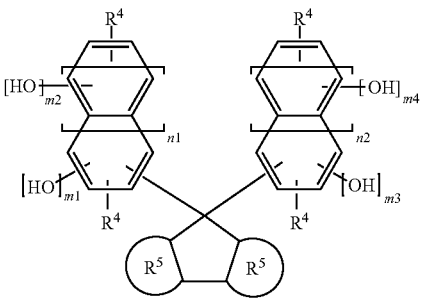

(2)

(In the formula, each $R^4$ independently represents a hydrogen atom or a hydrocarbon group having 6 to 20 carbon atoms; each $R^5$ independently represents a benzene ring or a naphthalene ring; m1 to m4 satisfy $1 \leq m1+m2 \leq 2$, and $1 \leq m3+m4 \leq 2$; and each n1 and n2 is 0 or 1.)

A-CHO (3)

(In the formula, A represents a hydrogen atom or a saturated or an unsaturated linear, branched or cyclic hydrocarbon group having 1 to 20 carbon atoms or an aromatic hydrocarbon group having 6 to 20 carbon atoms, optionally containing an ether group, a nitro group, a hydroxyl group and a chloro group.)

The resist underlayer film composition of the present invention preferably includes above-mentioned (C) a resin containing an aromatic ring which contains such a compound (C1), thereby enabling the thus formed resist underlayer film to be excellent in filling up a step of a substrate, to have solvent resistance and further to suppress generation of wiggling more effectively in etching a substrate, to make pattern roughness after etching favorable.

Further, the present invention provides a process for forming a resist underlayer film of a multilayer resist film used in lithography, wherein the resist underlayer film composition is coated on a substrate and the resist underlayer film composition is heat treated at the temperature of 200° C. or more and 600° C. or less for 10 to 600 sec to be cured, thereby forming the resist underlayer film.

As above, the resist underlayer film composition is coated and the resist underlayer film composition is heat treated at the temperature of 200° C. or more and 600° C. or less for 10 to 600 sec, thereby promoting a crosslinking reaction and preventing mixing thereof with the resist upper layer film or the resist intermediate layer film. In addition, part of a derivatization side chain of the fullerene derivative (A) in the resist underlayer film composition of the present invention is thermally decomposed in forming the underlayer film, thereby enabling to highly suppress generation of wiggling in etching.

Further, the present invention provides a process for forming a resist underlayer film of a multilayer resist film used in lithography, wherein the resist underlayer film composition is coated on a substrate and the resist underlayer film composition is baked in an atmosphere with an oxygen concentration of 0.1% or more and 21% or less to be cured, thereby forming the resist underlayer film.

The resist underlayer film composition of the present invention is baked in such an oxygen atmosphere, thereby enabling to obtain a fully cured resist underlayer film.

Further, the present invention provides a patterning process for forming a pattern on a substrate by lithography, comprising the steps of: at least, forming a resist underlayer film on the substrate by using the resist underlayer film composition;

forming a resist intermediate layer film on the resist underlayer film by using a resist intermediate layer film composition containing a silicon atom;

forming a resist upper layer film on the resist intermediate layer film by using a resist upper layer film composition composed of a photoresist composition, to form a multilayer resist film;

conducting exposure of a pattern circuit region of the resist upper layer film and then developing it by a developer to form a resist pattern in the resist upper layer film;

etching the resist intermediate layer film by using the pattern-formed resist upper layer film as a mask;

etching the resist underlayer film by using the pattern-formed resist intermediate layer film as a mask; and moreover, etching the substrate by using the pattern-formed resist underlayer film as a mask, to form a pattern on the substrate.

The patterning process using such a three-layer resist process enables to form a fine pattern on a substrate highly precisely, and the resist underlayer film composition of the present invention is suitable for such an underlayer film composition.

Further, etching of the resist underlayer film by using the resist intermediate layer film as a mask can be performed by using an etching gas mainly comprising an oxygen gas or a hydrogen gas.

Etching of the resist underlayer film by using the resist intermediate layer film as a mask can be performed by using an etching gas mainly comprising an oxygen gas or a hydrogen gas because a silicon-containing resist intermediate layer'film has an etching resistance to an oxygen gas or a hydrogen gas.

Further, the present invention provides a patterning process for forming a pattern on a substrate by lithography, comprising the steps of: at least, forming a resist underlayer film on the substrate by using the resist underlayer film composition;

forming an inorganic hard mask intermediate film selected from a silicon oxide film, a silicon nitride film and a silicon oxynitride film on the resist underlayer film;

forming a resist upper layer film on the inorganic hard mask intermediate film by using a resist upper layer film composition composed of a photoresist composition;

conducting exposure of a pattern circuit region of the resist upper layer film and then developing it by a developer to form a resist pattern in the resist upper layer film;

etching the inorganic hard mask intermediate film by using the obtained resist pattern as an etching mask;

etching the resist underlayer film by using the obtained inorganic hard mask intermediate film pattern as an etching mask; and etching the substrate by using the obtained resist underlayer film pattern as an etching mask, to form a pattern on the substrate.

Further, provided is a patterning process for forming a pattern on a substrate by lithography, comprising the steps of: at least, forming a resist underlayer film on the substrate by using the resist underlayer film composition;

forming an inorganic hard mask intermediate film selected from a silicon oxide film, a silicon nitride film and a silicon oxynitride film on the resist underlayer film;

forming an organic antireflection film on the inorganic hard mask intermediate film;

forming a resist upper layer film on the organic antireflection film by using a resist upper layer film composition composed of a photoresist composition;

conducting exposure of a pattern circuit region of the resist upper layer film and then developing it by a developer to form a resist pattern in the resist upper layer film;

etching the organic antireflection film and the inorganic hard mask intermediate film by using the obtained resist pattern as an etching mask;

etching the resist underlayer film by using the obtained inorganic hard mask intermediate film pattern as an etching mask; and etching the substrate by using the obtained resist underlayer film pattern as an etching mask, to form a pattern on the substrate.

As above, it is possible to form a photoresist film as the resist upper layer film on the resist intermediate layer film directly, and it is also possible to once form an organic anti-reflective film (BARC) by spin coating on the resist intermediate layer film and to subsequently form a photoresist film on the organic antireflective film. In the case of adopting a SiON film as the resist intermediate layer film, it is enabled to restrict reflection by virtue of the two-layer antireflective films, i.e., the SiON film and BARC film, even by a liquid immersion exposure at a higher NA exceeding 1.0. Another merit of the formation of the BARC resides in obtainment of an effect to decrease footing (trailing) of a photoresist pattern compared to a photoresist pattern just above the SiON film.

Further, the inorganic hard mask intermediate film can be formed by the CVD method or the ALD method.

The inorganic hard mask formed by the CVD method or the ALD method can be used in combination with the resist underlayer film formed by spin coating method because the resist underlayer film composition used in the present invention has a high thermal resistance to high temperature of 300° C. to 500° C.

Further, the present invention provides a fullerene derivative having $n^b$ partial structures represented by the following general formula (1b).

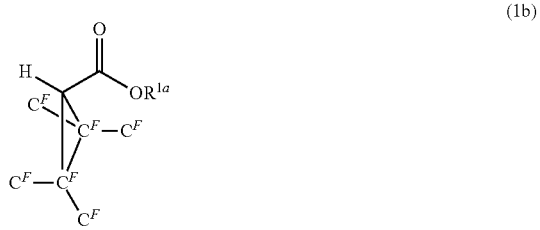

(1b)

(In the formula, $R^{1a}$ represents a substituted or an unsubstituted linear or cyclic tertiary alkyl group having 4 to 30 carbon atoms, optionally containing an unsaturated bond or an aromatic ring; $C^F$ represents a carbon atom constituting a fullerene skeleton; and $n^b$ represents an integer of 3 to 10.)

The fullerene derivative having $n^b$ partial structures represented by the foregoing general formula (1b) can be obtained by reacting fullerene with α-haloacetic acid ester in the presence of a base to form a three-membered ring together with HY-removal (Y: a halogen atom) reaction (dehydrohalogenation reaction).

The resist underlayer film composition having such a fullerene derivative used for a multilayer resist film enables to suppress pattern wiggling and to avoid the poisoning problem in forming an upper layer pattern.

As explained above, the resist underlayer film composition of the present invention enables to suppress pattern wiggling in forming, for example, an fine pattern of 40 nm or less and to avoid the poisoning problem in forming a resist upper layer pattern by using a chemically amplified resist, and extremely useful as a resist underlayer film composition for a multilayer resist process such as a silicon-containing two-layer resist process, a three-layer resist process using a silicon-containing intermediate film and a four-layer resist process using a silicon-containing intermediate layer film and an organic antireflection film.

BRIEF DESCRIPTION OF THE DRAWINGS

FIG. 1 is an explanatory view of a three-layer resist process.

DETAILED DESCRIPTION OF THE PREFERRED EMBODIMENTS

As mentioned above, heretofore, a resist underlayer film composition for forming a resist underlayer film which can suppress generation of wiggling in etching a substrate and avoid the poisoning problem in upper layer pattern formation using a chemically amplified resist has been required.

Accordingly, inventors of the present invention synthesized various fullerene derivatives soluble in a coating solvent (organic solvent) and investigated their properties. As a result, they found that the fullerene derivative mentioned later provides an effect to highly suppress generation of wiggling in etching by thermally decomposing part of a derivatization side chain which is necessary for dissolution, even if the fullerene derivative is a derivative which does not return to fullerene itself by baking and film-forming of an underlayer film. In addition, inventors of the present invention found that while the above effect is obtained, such a fullerene derivative does not affect resist pattern formation, that is, can avoid the poisoning problem, thereby succeeded in accomplishing the present invention.

That is, a resist underlayer film composition of the present invention includes (A) a fullerene derivative having a carboxyl group protected by a thermally labile group and (B) an organic solvent.

As a preferable embodiment of above-mentioned (A) a fullerene derivative having a carboxyl group protected by a thermally labile group, a fullerene derivative having n partial structures represented by the following general formula (1) is enumerated.

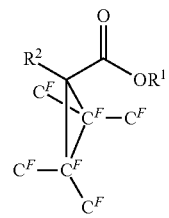

(1)

(In the formula, $R^1$ represents a thermally labile group; $R^2$ represents a hydrogen atom, a cyano group, —$COOR^3$, a linear, branched or cyclic alkyl group having 1 to 10 carbon atoms, an aryl group having 6 to 16 carbon atoms, a heteroaryl group having 4 to 16 carbon atoms or an aralkyl group having 7 to 20 carbon atoms, optionally containing a carbonyl group, an ether group, an ester group, a cyano group, a carboxyl group or a hydroxyl group; $R^3$ represents a hydrogen atom, $R^1$ or a linear, branched or cyclic alkyl group having 1 to 10 carbon atoms; $C^F$ represents a carbon atom constituting a fullerene skeleton of the fullerene derivative; and n represents an integer of 1 to 30.)

As a further preferable embodiment of above-mentioned (A) a fullerene derivative having a carboxyl group protected by a thermally labile group, a fullerene derivative having n partial structures represented by the following general formula (1a) is enumerated.

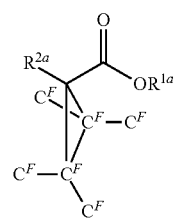

(1a)

(In the formula, $R^{1a}$ represents a substituted or an unsubstituted linear or cyclic tertiary alkyl group having 4 to 30 carbon atoms, optionally containing an unsaturated bond or an aromatic ring; $R^2$ represents a hydrogen atom, a cyano group, —$COOR^{3a}$, a methyl group, an ethyl group, an acetyl group, a phenyl group, a naphthyl group, a furyl group, a benzoyl group or a naphthoyl group; $R^{3a}$ represents a hydrogen atom, $R^{1a}$ or a linear, branched or cyclic alkyl group having 1 to 10 carbon atoms; $C^F$ represents a carbon atom constituting a fullerene skeleton of the fullerene derivative; and n represents an integer of 1 to 30.)

The resist underlayer film composition of the present invention can include a single kind of the fullerene derivative having n partial structures (n is an integer of 1 to 30) represented by the foregoing general formula (1) or particularly the foregoing general formula (1a), or a mixture of two or more kinds of the fullerene derivatives having a different n value from each other. Among them, advantageous is the one including a mixture of two or more kinds of the fullerene derivatives in view of a solubility to a resist solvent and film formability. In this case, it is particularly preferable that the n value of the fullerene derivative having the highest presence ratio is an integer of 3 to 10. It is preferable that n is 3 or more because there is no possibility of deterioration of the solubility to a resist solvent and film formability, while it is preferable that n is 10 or less because there is no possibility of deterioration of the above-mentioned wiggling suppressing effect.

Further, the present invention provides a fullerene derivative having $n^b$ partial structures represented by the following general formula (1b).

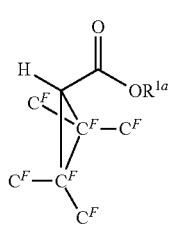

(1b)

(In the formula, $R^{1a}$ represents a substituted or an unsubstituted linear or cyclic tertiary alkyl group having 4 to 30 carbon atoms, optionally containing an unsaturated bond or an aromatic ring; $C^F$ represents a carbon atom constituting a fullerene skeleton; and $n^b$ represents an integer of 3 to 10.)

In the foregoing general formulae (1), (1a) and (1b), $C^F$ represents a carbon atom constituting a fullerene skeleton. Fullerene consists of only carbon atoms, in which a plurality of five-membered ring and six-membered ring composes a carbon network possessing a closed shell and each carbon atom is bonded to other three carbon atoms, and $C^F$ represents each of six adjacent carbon atoms in the fullerene skeleton.

Fullerene usually has 60 or more and 120 or less carbon atoms. Specifically, $C_{60}$, $C_{70}$, $C_{76}$, $C_{78}$, $C_{84}$, $C_{90}$ and the like are enumerated. Shown below is a fullerene skeleton of fullerene $C_{60}$. Meanwhile, in the following formula, a single bond and a double bond are not distinguished, and both are represented by a solid line or a broken line.

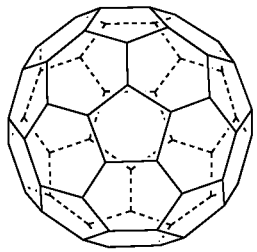

Fullerene $C_{60}$ Skeleton

In the foregoing general formula (1), $R^1$ represents a thermally labile group and the thermally labile group is not particularly limited structurally as long as it is decomposed by heating at the temperature of 50° C. to 400° C. to generate a carboxyl group, in which $R^1$ is a hydrogen atom. Preferable is $R^{1a}$ mentioned later (a tertially alkyl group), a 1-alkoxyalkyl group (an acetal) having 2 to 30 carbon atoms, a β-heteroatom-substituted alkyl group having 2 to 30 carbon atoms or a γ-carbonylalkyl group having 3 to 30 carbon atoms, and particularly preferable is $R^{1a}$ (a tertially alkyl group).

Decomposition starting temperature of $R^1$ is more preferably 80° C. to 300° C. or further preferably 100° C. to 250° C. because in a case of 80° C. or more, there is no possibility of deterioration of a storage stability of the underlayer film composition and in a case of 300° C. or less, there is no possibility of deterioration of the above-mentioned wiggling suppressing effect. The presence of $R^1$ is effective to secure a solubility of the fullerene derivative to the solvent for the underlayer film, and has a function to reduce the substantial hydrogen concentration of the underlayer film by being decomposed and removed in formation of the underlayer film and a heat treatment. In addition, due to the structure of $R^1$, a substance generated by the decomposition of $R^1$ is not a basic compound such as amine, thereby enabling to suppress an adverse effect on a pattern profile in patterning of the upper resist.

When $R^1$ is a 1-alkoxyalkyl group having 2 to 30 carbon atoms, more specific examples of $R^1$ include methoxymethyl, ethoxymethyl, isopropoxymethyl, cyclohexyloxymethyl, 2-adamantyloxymethyl, 1-octadecyloxymethyl, 1-methoxyethyl, 1-ethoxyethyl, 1-butoxyethyl, 1-cyclohexyloxyethyl, 1-methoxypropyl, 1-ethoxypropyl, 1-methoxy-2-methylpropyl, 1-ethoxy-2-methylpropyl, 1-cyclohexyloxy-2-methylpropyl, 2-methyl-1-(8-tricyclo[5.2.1.0$^{2,6}$]decyloxy)propyl, 1-methoxy-1-methylethyl, 2-tetrahydrofuranyl and 2-tetrahydro-2H-pyranyl. When $R^1$ is a β-heteroatom-substituted alkyl group having 2 to 30 carbon atoms, more specific examples of $R^1$ include 2-methoxyethyl, 2-chloroethyl, 2-bromoethyl, 2,2,2-trichloroethyl, 2-hydroxyethyl, 2-(2-methoxyethoxy)ethyl, 2-[2-(2-methoxyethoxy)ethoxy]ethyl, 2-acetoxyethyl, 2-methylthioethyl, 2-(p-toluenesulfonyloxy)ethyl, 2-methoxycyclohexyl, 2-methoxypropyl, $HOCH_2CH_2OCH_2CH_2$—, $HO(CH_2CH_2O)_2CH_2CH_2$—, $HO(CH_2CH_2O)_3CH_2CH_2$—, $HO(CH_2CH_2O)_4CH_2CH_2$—, $HO(CH_2CH_2O)_5CH_2CH_2$—, $HO(CH_2CH_2O)_6CH_2CH_2$—, $HO(CH_2CH_2O)_7CH_2CH_2$—, $HO(CH_2CH_2O)_8CH_2CH_2$—, $HO(CH_2CH_2O)_8CH_2CH_2$—, $HO(CH_2CH_2O)_{10}CH_2CH_2$—, $HO(CH_2CH_2O)_{11}CH_2CH_2$—, $HO(CH_2CH_2O)_{12}CH_2CH_2$—, $HO(CH_2CH_2O)_{13}CH_2CH_2$— and $HO(CH_2CH_2O)_{14}CH_2CH_2$—. When R is a γ-carbonylalkyl group having 3 to 30 carbon atoms, more specific examples of $R^1$ include 2-cyanoethyl, cyanopropyl, 2-cyanocyclohexyl, 3-oxobutyl, 3-oxopentyl, 3-oxocyclohexyl, 2-methoxycarbonylethyl, 2-ethoxycarbonylethyl, 2-methoxycarbonylpropyl and 5-oxo-3-tetrahydrofuranyl.

In the foregoing general formulae (1a) and (1b), $R^{1a}$ represents a linear or cyclic tertiary alkyl group having 4 to 30 carbon atoms, optionally containing an unsaturated bond or an aromatic ring. $R^{1a}$ may be a substituted or unsubstituted tertiary alkyl group, and part of methylene groups thereof may be substituted with an oxygen atom or part of hydrogen atoms thereof may be substituted with a hydroxyl group. Specific examples of the partial structure —O—$R^{1a}$ in the foregoing general formulae (1a) and (1b) include the following structures, but are not limited to thereto.

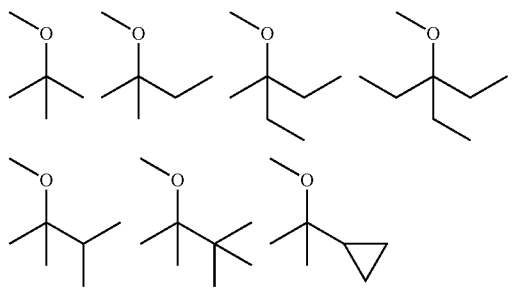

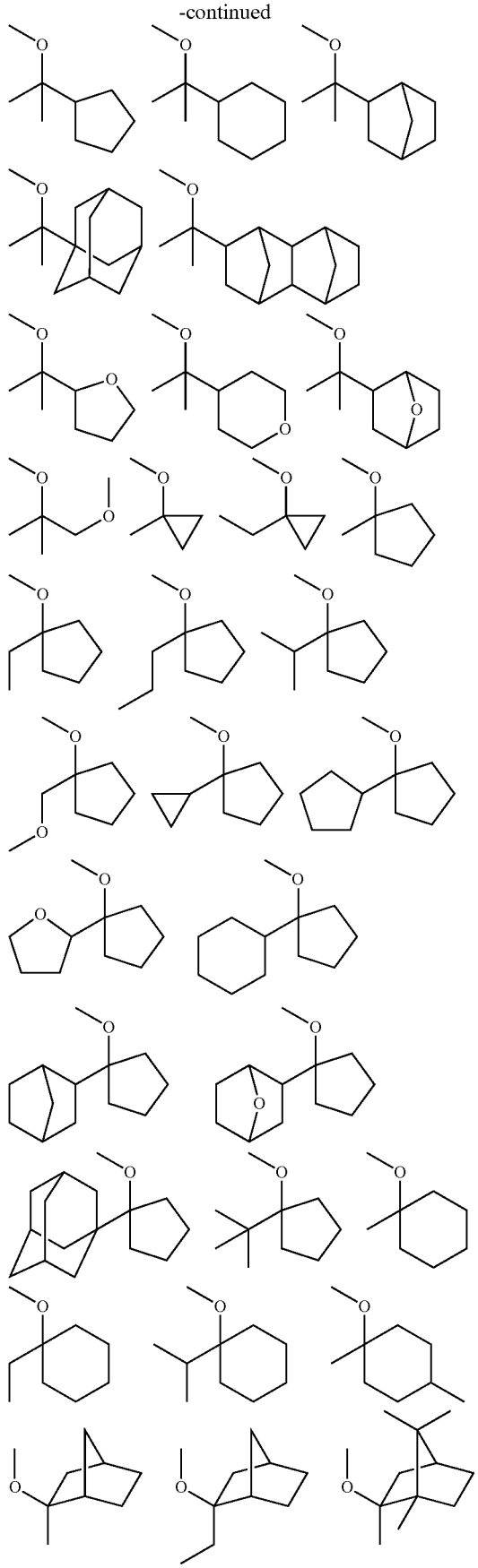
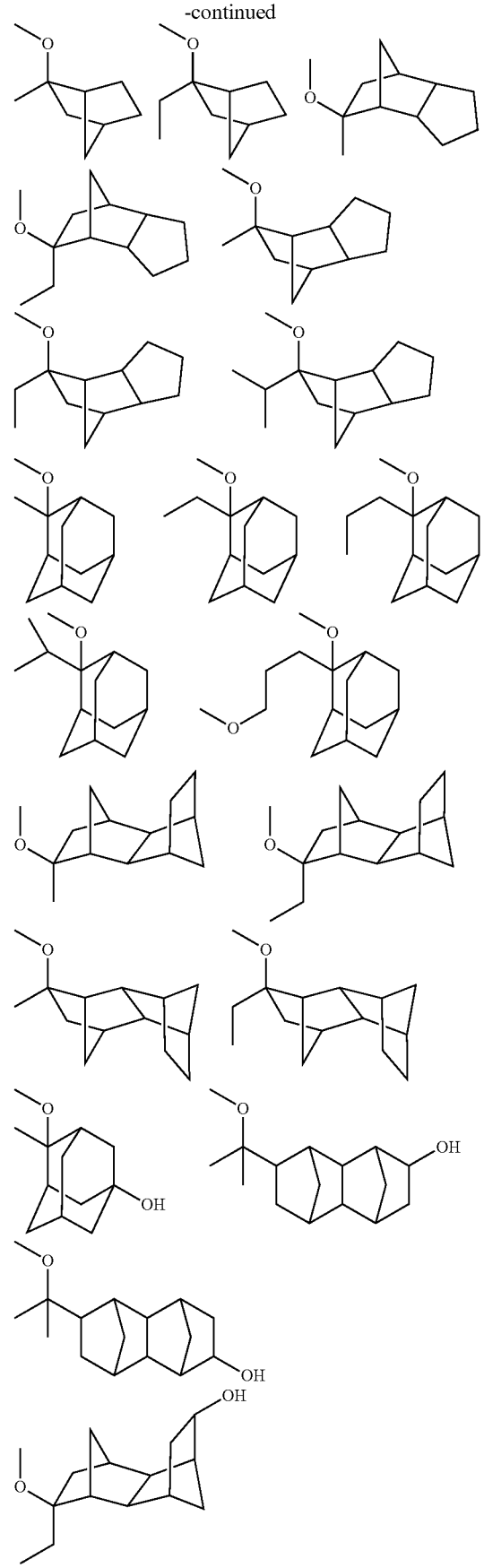

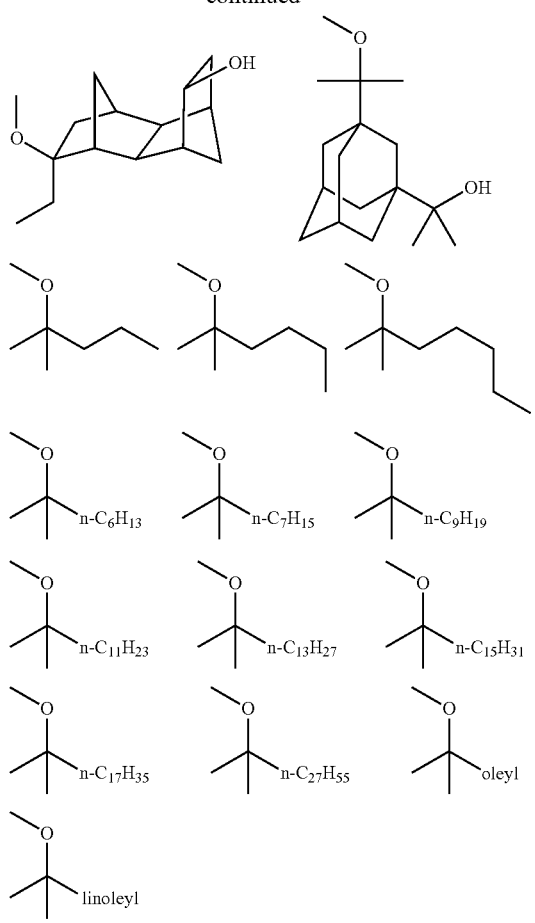

(In the formula, "oleyl" represents an oleyl group and "linoleyl" represents a linoleyl group.)

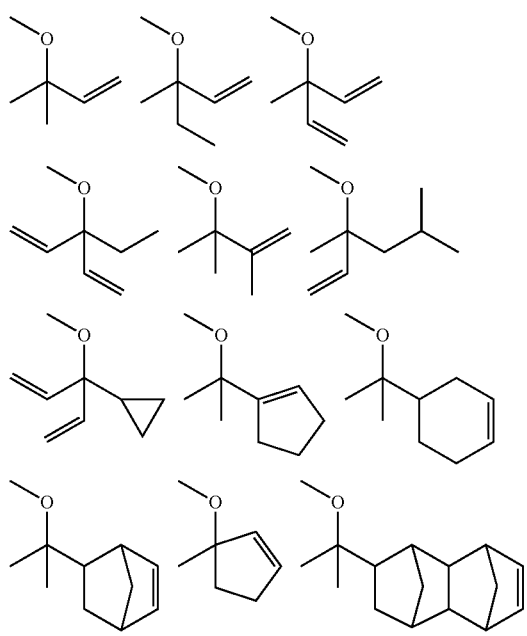

In the formula (1), $R^2$ represents a hydrogen atom, a cyano group, —$COOR^3$, a linear, branched or cyclic alkyl group having 1 to 10 carbon atoms, an aryl group having 6 to 16 carbon atoms, a heteroaryl group having 4 to 16 carbon atoms or an aralkyl group having 7 to 20 carbon atoms, optionally containing a carbonyl group, an ether group, an ester group, a cyano group, a carboxyl group or a hydroxyl group; $R^3$ represents a hydrogen atom, $R^1$ or a linear, branched or cyclic alkyl group having 1 to 10 carbon atoms. More specific examples of $R^2$ include a hydrogen atom, cyano, methyl, ethyl, propyl, allyl, homoallyl, isopropyl, butyl, sec-butyl, tert-butyl, tert-amyl, pentyl, hexyl, cyclopentyl, cyclohexyl, norbornyl, adamantyl, vinyl, isopropenyl, propenyl, methallyl, ethynyl, acetyl, propionyl, methoxymethyl, methoxycarbonylmethyl, cyanomethyl, carboxymethyl, 2-hydroxyethyl, phenyl, tolyl, xylyl, naphthyl, indanyl, indenyl, anthranyl, phenanthryl, pyrenyl, naphthacenyl, acetoxyphenyl, methoxyphenyl, methoxycarbonylphenyl, cyanophenyl, carboxyphenyl, hydroxyphenyl, hydroxynaphthyl, methoxynaphthyl, furanyl, thiophenyl, benzofuranyl, benzothiophenyl, phenoxathiinyl, benzyl, 2-phenylethyl, 3-phenylpropyl, naphthylmethyl, pyrenylmethyl, 2-phenylvinyl, 1-phenylvinyl, phenylethynyl, methoxycarbonyl, ethoxycarbonyl, propoxycarbonyl, butoxycarbonyl, isopropoxycarbonyl, cyclohexyloxycarbonyl, adamantyloxycarbonyl and —$COOR^1$.

As $R^2$, $R^{2a}$ is more preferable. $R^{2a}$ represents a hydrogen atom, a cyano group, —$COOR^{3a}$, a methyl group, an ethyl group, an acetyl group, a phenyl group, a naphtyl group, a furyl group, a benzoyl group or a naphthoyl group. $R^{3a}$ represents a hydrogen atom, $R^{1a}$, or a linear, branched or cyclic alkyl group having 1 to 10 carbon atoms. When $R^{2a}$ is —$COOR^{3a}$, more specific examples of $R^{3a}$ include a methyl group, an ethyl group, a propyl group, an isopropyl group, a butyl group, a sec-butyl group, a pentyl group, a hexyl group, a cyclopentyl group, a cyclohexyl group, a norbornyl group, an adamantyl group and $R^{1a}$. In view of ease of manufacture, a hydrogen atom is particularly preferable as $R^2$. Meanwhile, in addition to the partial structure represented by the foregoing general formula (1) or particularly the foregoing general formula (1a), the fullerene derivative used for the resist underlayer film composition of the present invention may have other functional groups such as an epoxide, a hydroxyl group and an amino group on the fullerene skeleton in the range not diminishing the effect of the present invention.

More specific examples of the fullerene derivative having a partial structure represented by the general formulae (1), (1a) or (1b) include the following compounds, but are not limited thereto. In the formula, n represents the same as before (in the case of the fullerene derivative having the partial structure represented by the general formula (1b), n in the following compound corresponds to $n^b$); each l and m is an integer satisfying $l+m=n$;

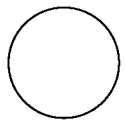

represents a fullerene skeleton; $Bu^t$ represents a tert-butyl group; Ph represents a phenyl group; Me represents a methyl group; and Et represents an ethyl group, and hereinafter, these symbols represent the same as above.

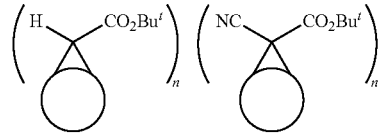

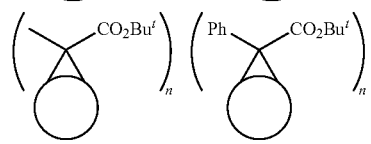

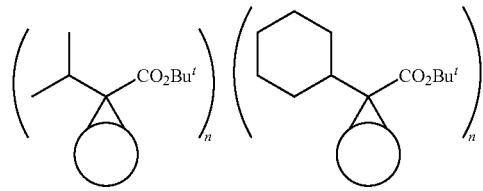

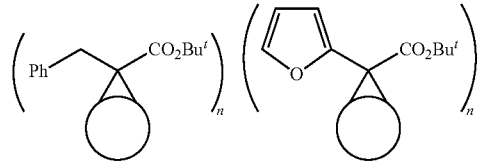

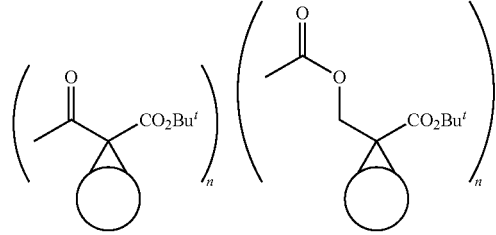

-continued

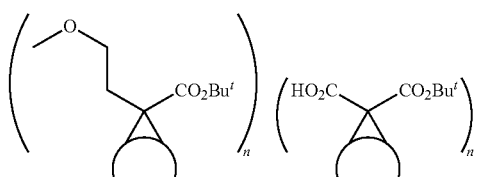

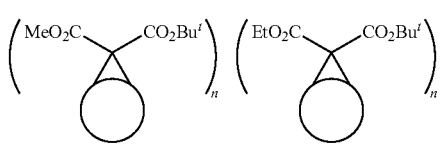

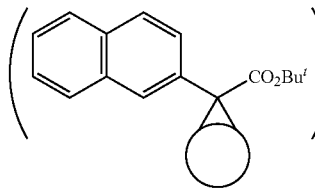

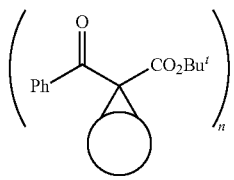

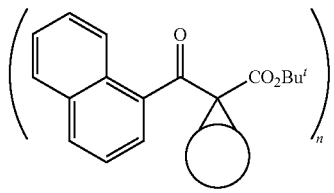

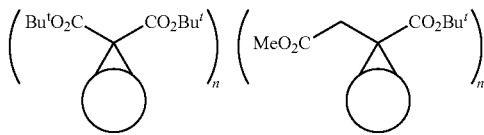

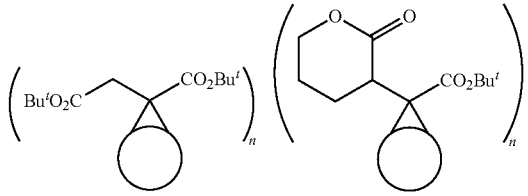

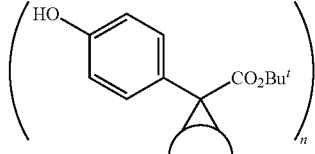

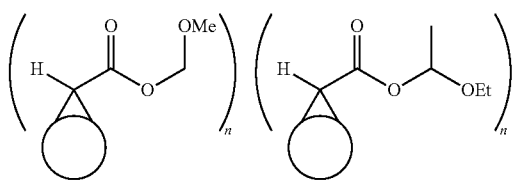

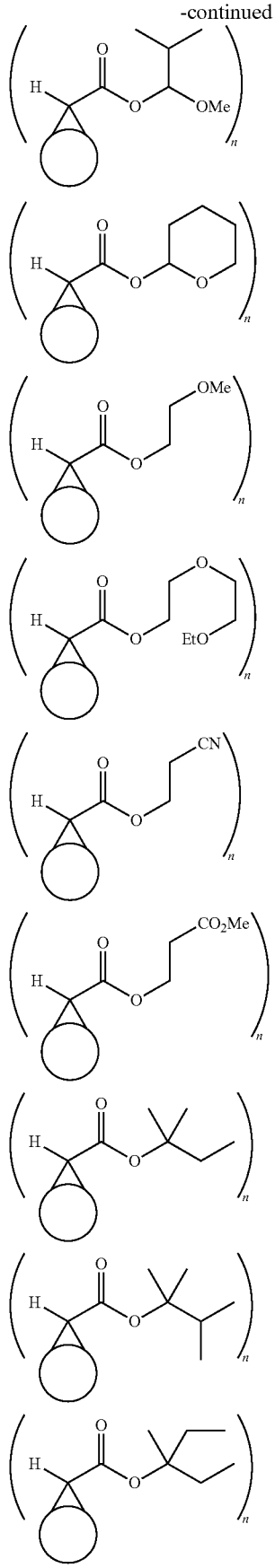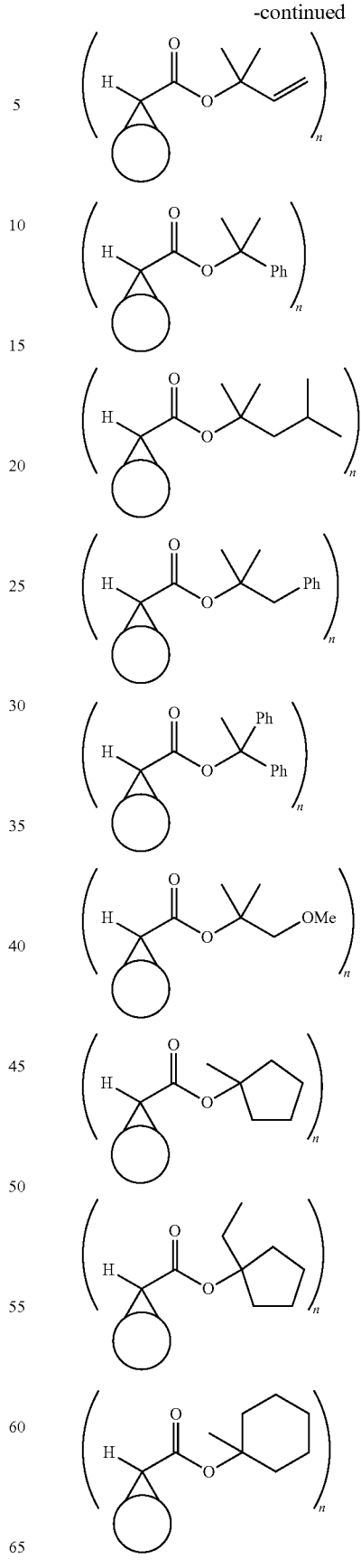

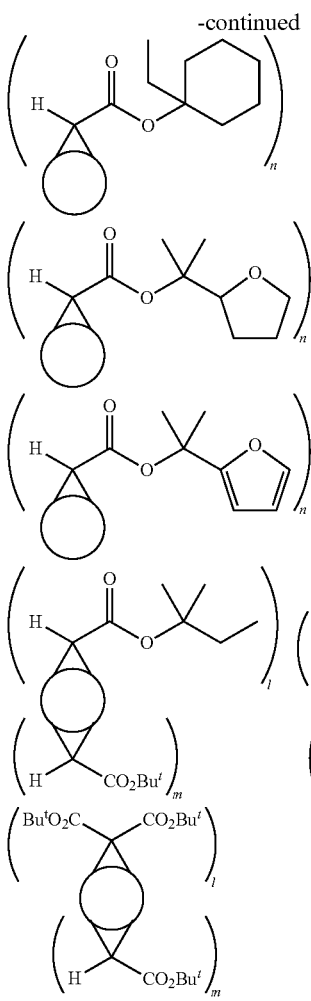

A blending amount of the fullerene derivative having a carboxyl group protected by a thermally labile group, that is, the fullerene derivative having a partial structure represented by the general formula (1), (1a) or (1b), into a resist underlayer film composition is preferably 10 parts by mass or more and 85 parts by mass or less, or more preferably 15 parts by mass or more and 75 parts by mass or less in 100 parts by mass of all solid components of the resist underlayer film composition except for an organic solvent. 10 parts by mass or more is preferable because a wiggling resistance is more sufficient, while 85 parts by mass or less is preferable because there is no possibility of deterioration of uniformity of a coated film or generation of a crack.

The fullerene derivative having a carboxyl group protected by a thermally labile group, that is, the fullerene derivative having a partial structure represented by the general formula (1), (1a) or (1b) can be manufactured by selecting an optimum manufacturing process corresponding to the structure thereof. More specifically, for example, the fullerene derivative having a carboxyl group protected by a thermally labile group, that is, the fullerene derivative (4) having a partial structure represented by the general formula (1), (1a) or (1b) can be manufactured by such a method shown below according to each reaction disclosed in: Adv. Funct. Mater., vol. 2009, 779; Angew. Chem. Int. Ed. Engl., vol. 33, 437 (1994); Angew. Chem. Int. Ed. Engl., vol. 34, 1607 (1995); Angew. Chem. Int. Ed. Engl., vol. 35, 2101 (1996); Chem. Ber., vol. 126, 1957 (1993); Chem. Eur. J., vol. 3, 561 (1997); Chem. Lett., vol. 1997, 1037; Helv. Chim. Acta, vol. 76, 1231 (1993); Helv. Chim. Acta, vol. 78, 1334 (1995); Helv. Chim. Acta, vol. 78, 1673 (1995); Helv. Chim. Acta, vol. 79, 736 (1996); Helv. Chim. Acta, vol. 79, 1741 (1996); J. Am. Chem. Soc., vol. 116, 9385 (1994); J. Chem. Soc. Perkin 1, vol. 1997, 1595; Liebigs Ann., vol. 1995, 1551; Tetrahedron Lett., vol. 36, 5707 (1995); Tetrahedron Lett., vol. 36, 6843 (1995); Tetrahedron Lett., vol. 39, 2731 (1998); and Tetrahedron Lett., vol. 39, 2747 (1998).

In the following general formulae, X represents an elimination group such as a halogen atom, SBU represents 1,8-diazabycyclo[5.4.0]undeca-7-ene, Ts represents a p-toluenesulfonyl group, and hereinafter, these symbols represent the same as above. $R^1$, $R^2$ and

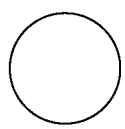

represent the same as before.

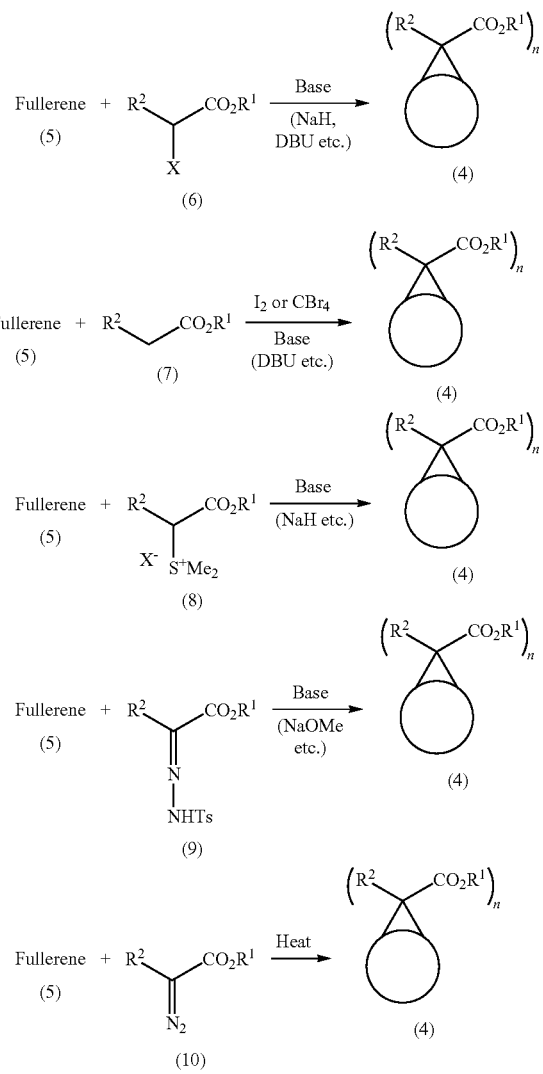

As fullerene (5) used in the above reaction, as mentioned above, $C_{60}$ or $C_{70}$ may be used solely, and a mixture of $C_{60}$ and $C_{70}$ and a mixed fullerene further containing higher fullerenes in addition to $C_{60}$ and $C_{70}$ may also be used.

In addition, the fullerene derivative (4) can also be manufactured by using a compound (II), which can be manufactured in a similar way mentioned above as an intermediate compound and by performing a deprotection reaction (an intermediate compound (12)) and a reprotection reaction as shown in the following reaction formula according to a usual manner described in, for example, Protective Groups in Organic Synthesis, 3rd Ed., Wiley-Interscience, New York, 1999, 373-378. However, it is estimated that manufacturing cost increases along with increase of number of steps, and therefore, this manufacturing process is disadvantageous to industrialization. In the following general formula, P represents a protective group and n, $R^1$, $R^2$ and

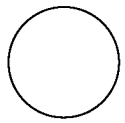

represent the same as before.

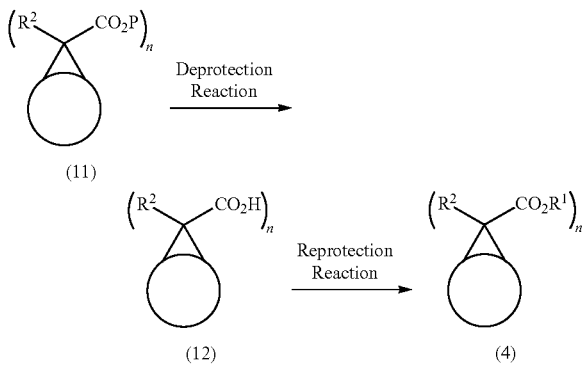

Especially, the fullerene derivative (4b) having a partial structure represented by the foregoing general formula (1b) can be easily manufactured by the method shown below. Meanwhile, in the present invention, the manufacturing method is not limited thereto. In the following general formula, Y represents a halogen atom and $n^b$, $R^{1a}$ and

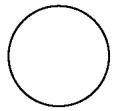

represent the same as before.

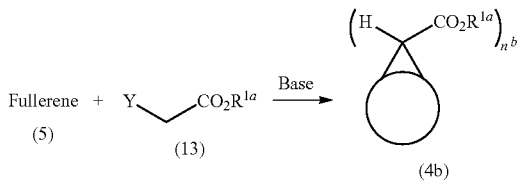

That is, in the synthesis method of the fullerene derivative (4b) having a partial structure represented by the formula (1b), the fullerene derivative (4b) can be obtained by reacting fullerene (5) with α-haloacetic acid ester (13) in the presence of a base to form a three-membered ring together with HY-removal reaction (dehydrohalogenation reaction). The reaction is carried out by mixing fullerene (5), α-haloacetic acid ester (13) and the base in a solvent and as appropriate, by cooling or heating.

As for fullerene (5), $C_{60}$ or $C_{70}$ may be used solely, and a mixture of $C_{60}$ and $C_{70}$ and a mixed fullerene further containing higher fullerenes in addition to $C_{60}$ and $C_{70}$ may also be used. In addition, α-haloacetic acid ester (13) may be prepared by using commercially available one or by manufacturing it according to a known usual manner (for example, a method described in Japanese Patent Laid-Open (kokai) No. 2005-331918).

As a halogen atom Y in the foregoing general formula (13), chlorine, bromine and iodine are preferable. In view of ease of manufacture and reaction selectivity of the above-mentioned three-membered ring formation reaction, more preferable are chlorine and bromine, and the most preferable is chlorine. The optimum amount of α-haloacetic acid ester (13) to be used changes depending on the $n^b$ value to be set, but preferable is $n^b \times 0.2$ to $n^b \times 5.0$ mole or particularly $n^b \times 0.5$ to $n^b \times 2.0$ mole relative to 1 mole of fullerene (5).

As a solvent, one kind or a mixture of two or more kinds selected from aliphatic hydrocarbons such as hexane and heptane; aromatic hydrocarbons such as toluene, xylene, trimethylbenzene and methylnaphthalene; ethers such as dibuthyl ether, diethylene glycol diethyl ether, diethylene glycol dimethyl ether and tetrahydrofuran; ketones such as acetone and 2-butanone; alcohols such as methanol, ethanol, 2-propanol, t-butylalcohol, methoxyethanol and diethylene glycol monomethyl ether; esters such as ethyl acetate; nitriles such as acetonitrile; amides such as N,N-dimethylformamide and N,N-dimethylacetamide; halogenated hydrocarbons such as o-dichlorobenzene, dichloromethane and 1,2-dichloroethane; and water may be used, and it is more preferable to use aromatic hydrocarbons and a mixed solvent containing them in view of securing a solubility of fullerene (5) of starting materials.

As a base, one kind or a mixture of two or more kinds selected from metal hydroxides such as sodium hydrate and potassium hydrate; metal alkoxides such as sodium methoxide and potassium t-butoxide; metal hydrides such as sodium hydride; metal-organics such as butyllithium and ethyl magnesium bromide; metal salts such as potassium carbonate and sodium carbonate; organic basic compounds such as pyridine, triethylamine and DBU may be used. An adding amount of the basic compounds is preferably 0.2 to 5 moles or particularly 0.5 to 2.0 moles relative to 1 mole of α-haloacetic acid ester (13).

A reaction temperature of the above-mentioned three-membered ring formation reaction is preferably about 0° C. to about the boiling point of the solvent, and an appropriate reaction temperature for each reaction condition is selected. For increasing yields, the reaction time of the three-membered ring formation reaction is desirably determined by monitoring the progress of the reaction by thin-layer chromatography, liquid chromatography or the like, but it is usually about 0.5 to about 100 hours. At the end of reaction, the intended substance, the fullerene derivative (4b) having a partial structure represented by the foregoing general formula (1b), is obtained by a conventional aqueous workup and/or a filtration treatment of undissolved substances. The fullerene derivative (4b) can also be purified by any conventional technique such as crystallization and chromatography as appropriate.

An organic solvent (B) usable for the resist underlayer film composition of the present invention is not particularly limited as long as a fullerene derivative of the (A) component can dissolve therein, but preferable is an organic solvent in which an aromatic ring-containing resin mentioned later, a phenolic hydroxyl group-containing compound, an acid generator, a crosslinker, a surfactant and the like can dissolve. Specifically, a solvent described in paragraphs [0091] to [0092] of Japanese Patent Laid-Open (kokai) No. 2007-199653 can be added.

Further, it is preferable that the resist underlayer film composition of the present invention includes (C) a resin containing an aromatic ring to improve film formability in spin coating, a filling-up characteristic of a stepped substrate and an etching resistance.

Such a resin preferably includes a compound (C1) obtained by a polycondensation reaction between a compound represented by the following general formula (2) and a compound represented by the following general formula (3) under an acid condition.

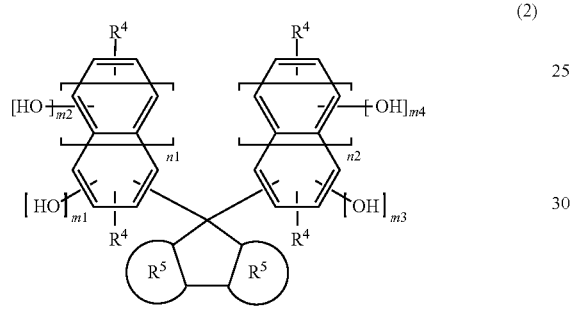

(2)

(In the formula, each $R^4$ independently represents a hydrogen atom or a hydrocarbon group having 6 to 20 carbon atoms; each $R^5$ independently represents a benzene ring or a naphthalene ring; m1 to m4 satisfy $1 \leq m1+m2 \leq 2$, and $1 \leq m3+m4 \leq 2$; and each n1 and n2 is 0 or 1.)

A-CHO         (3), (In the formula, A represents a hydrogen atom or a saturated or an unsaturated linear, branched or cyclic hydrocarbon group having 1 to 20 carbon atoms or an aromatic hydrocarbon group having 6 to 20 carbon atoms, optionally containing an ether group, a nitro group, a hydroxyl group and a chloro group.)

Specifically, the following are exemplified as a compound represented by the general formula (2).

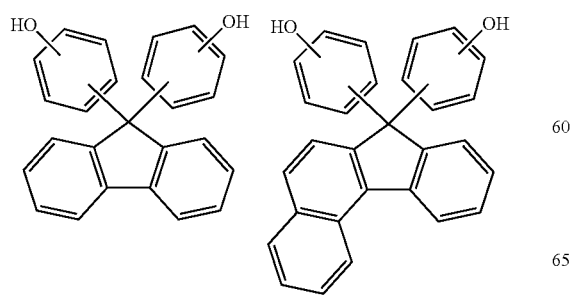

-continued

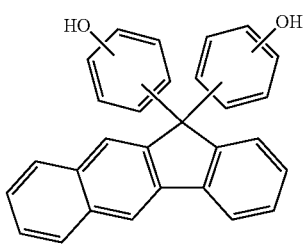

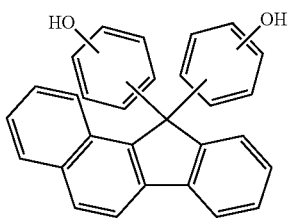

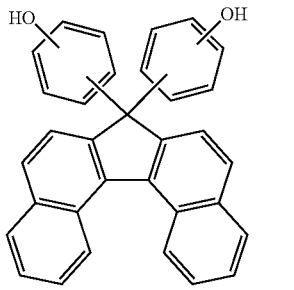

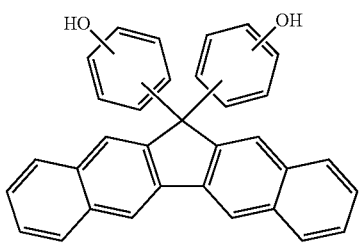

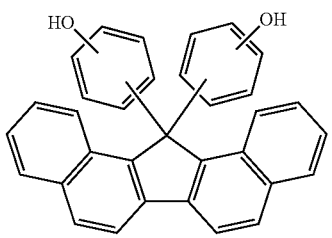

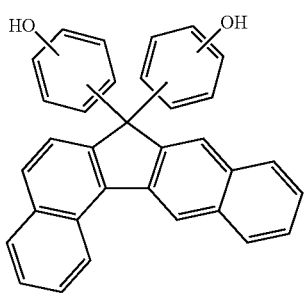

-continued
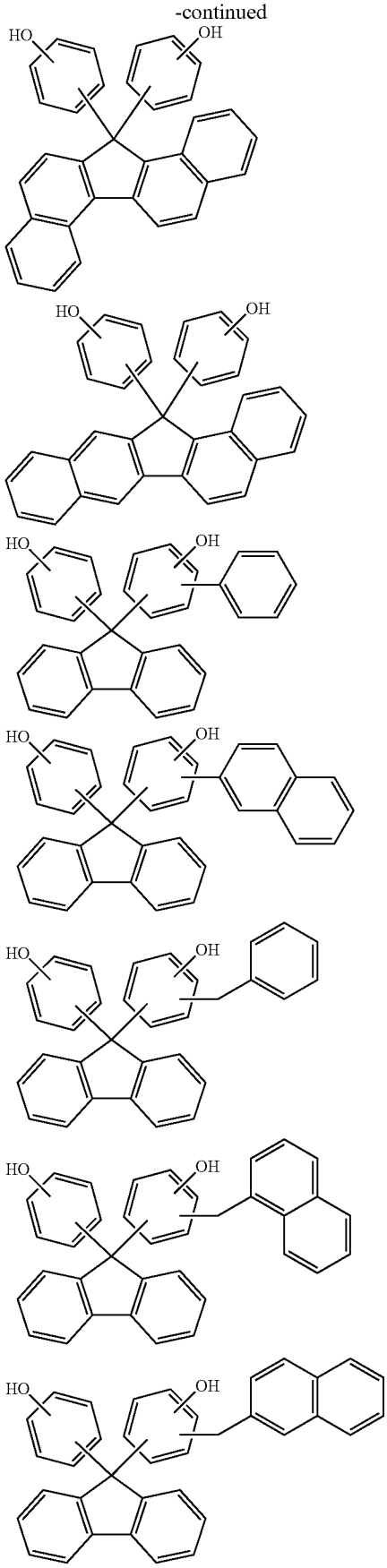
-continued
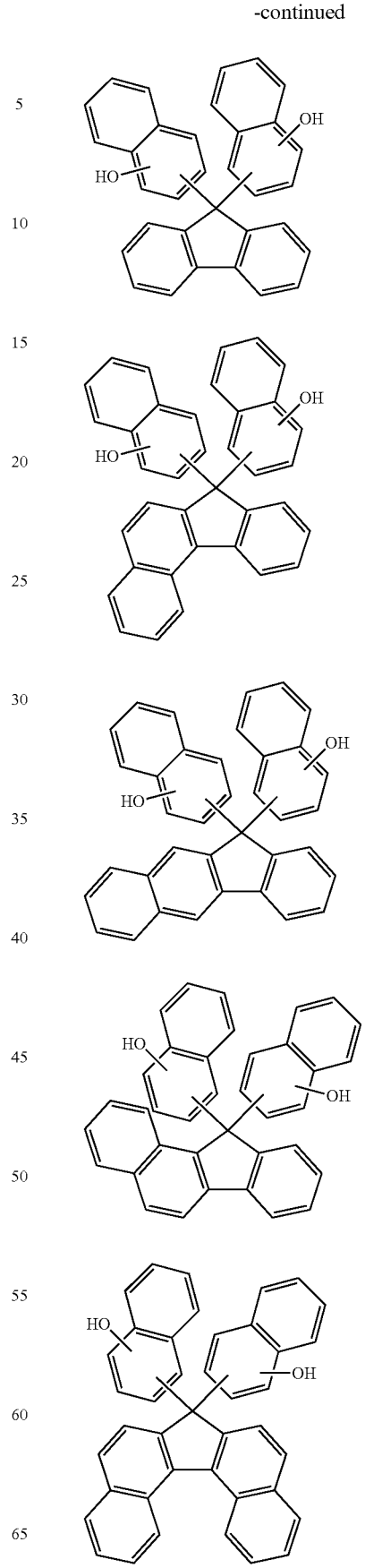

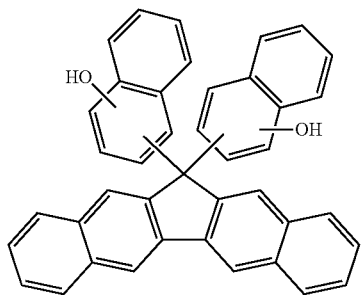
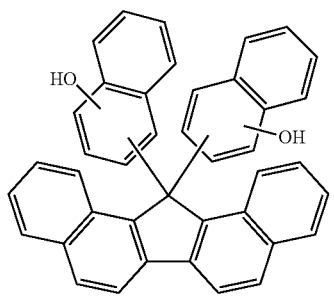
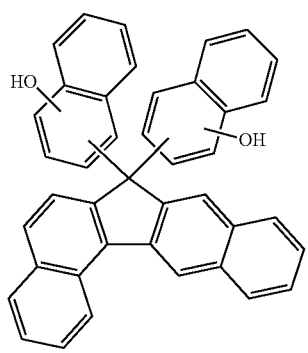
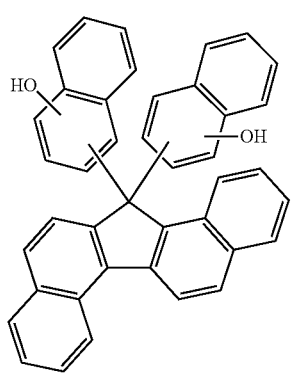
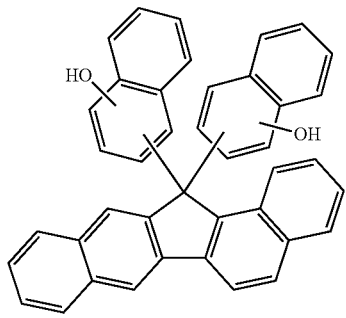
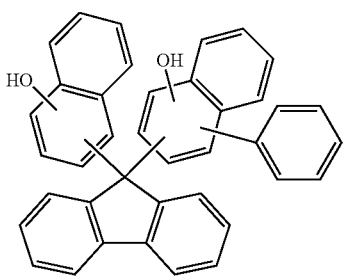
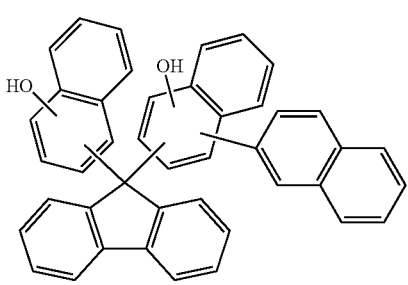
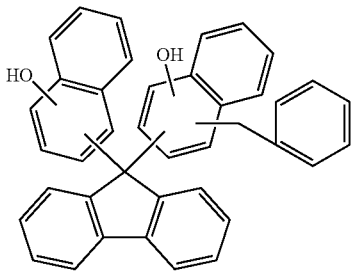
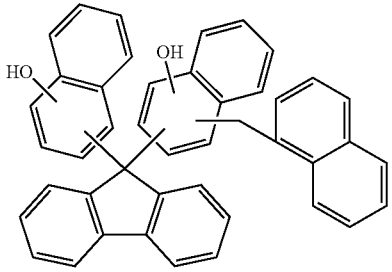
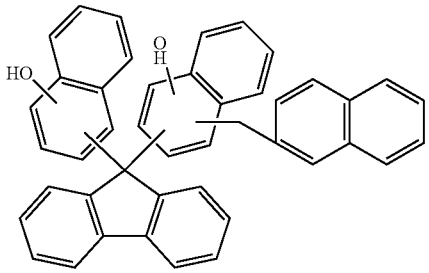
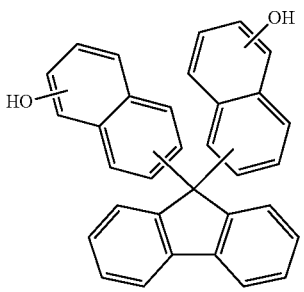

-continued
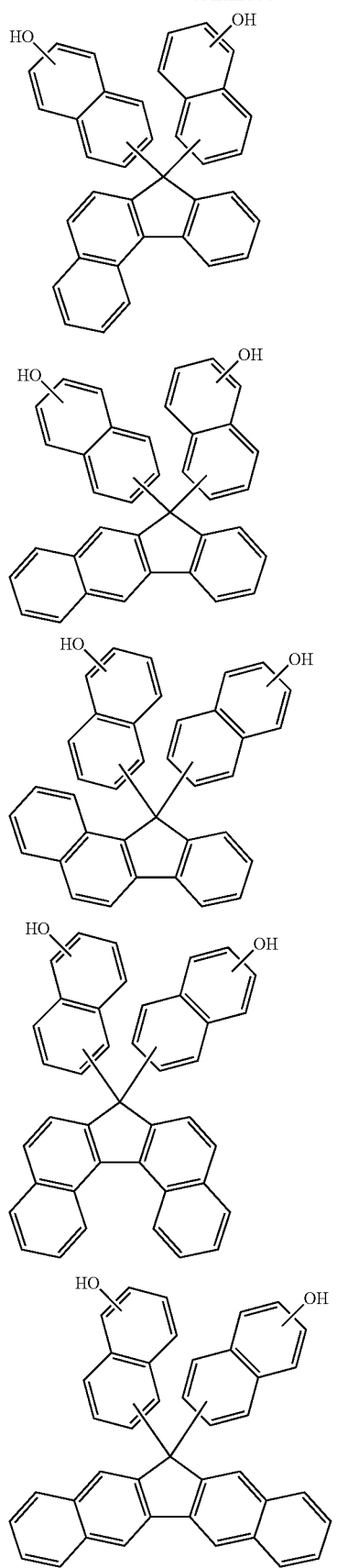
-continued
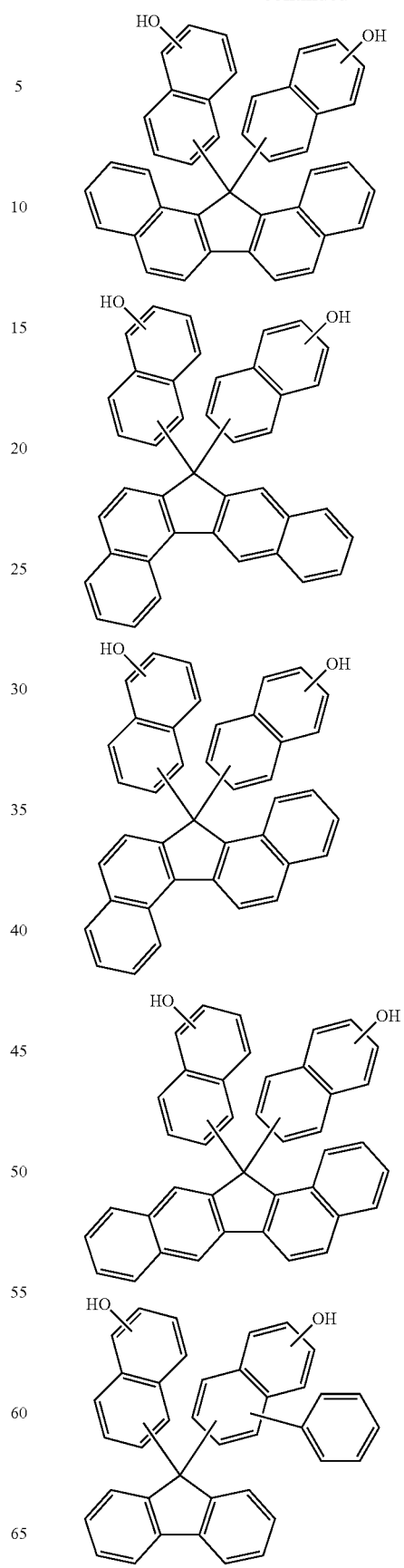

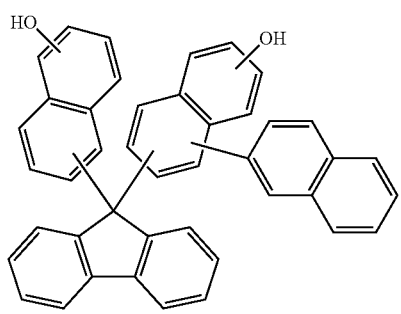
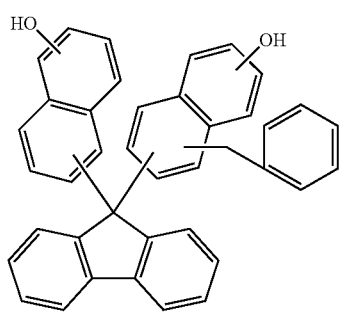
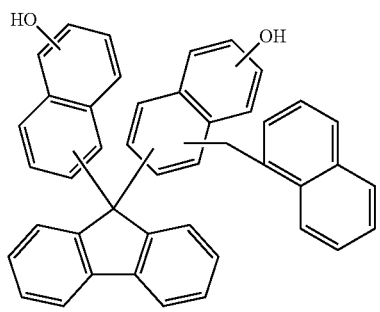
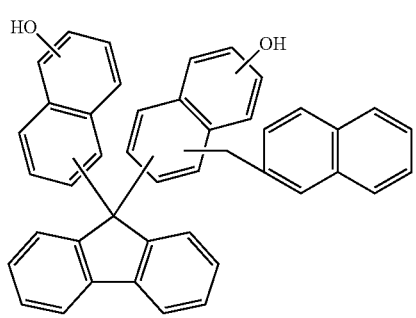
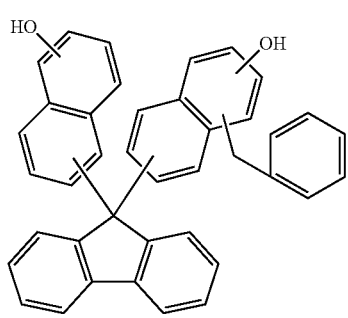
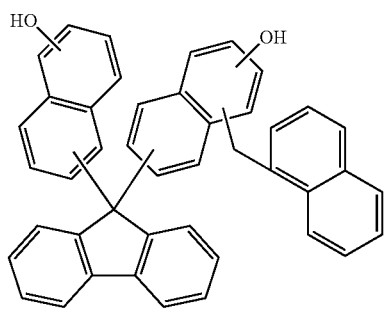
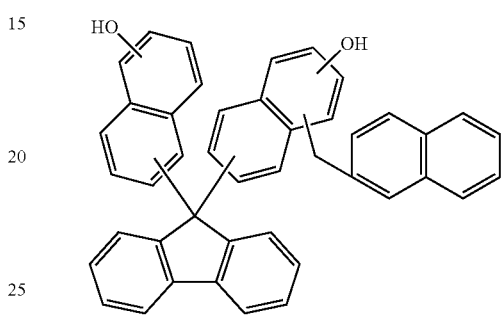
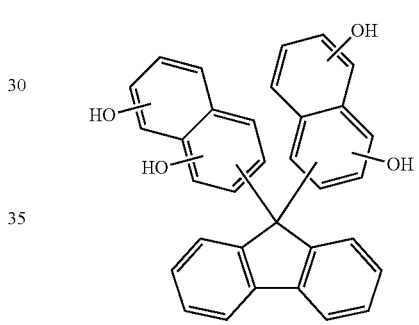
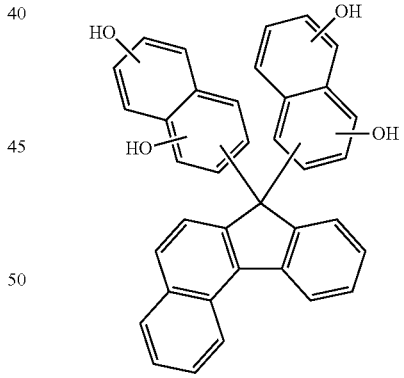
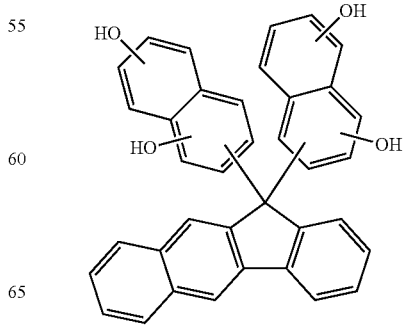

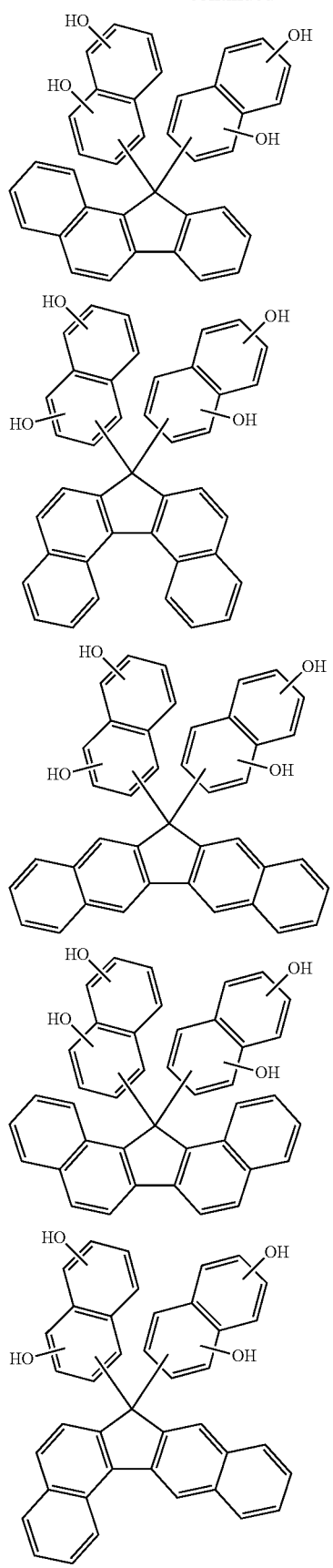
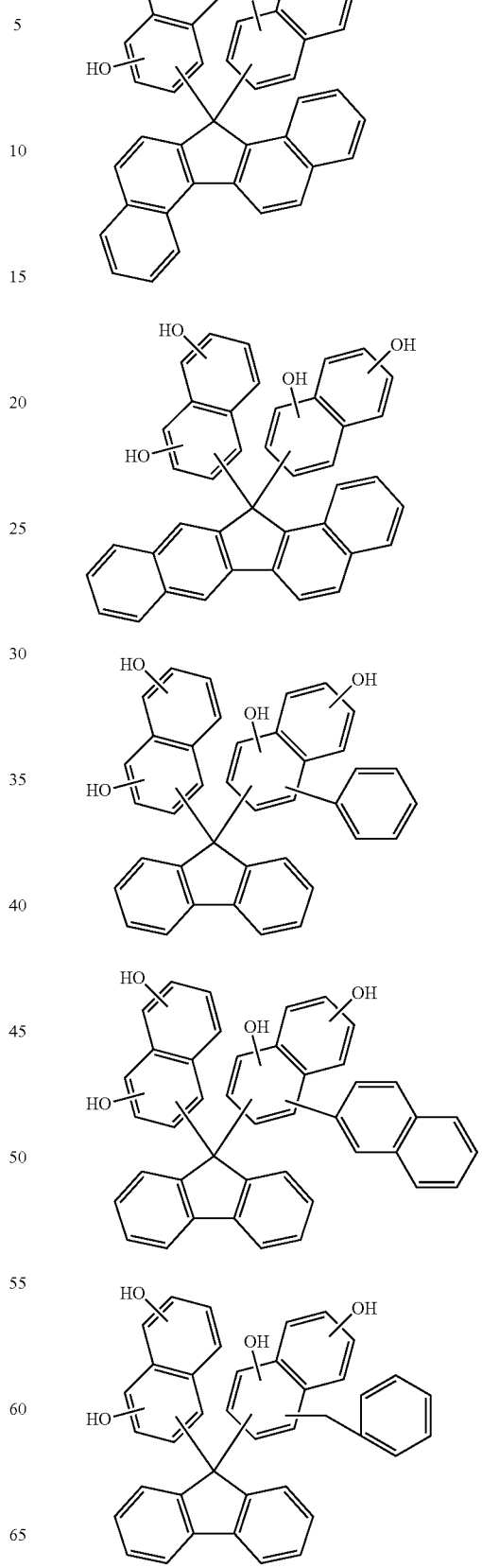

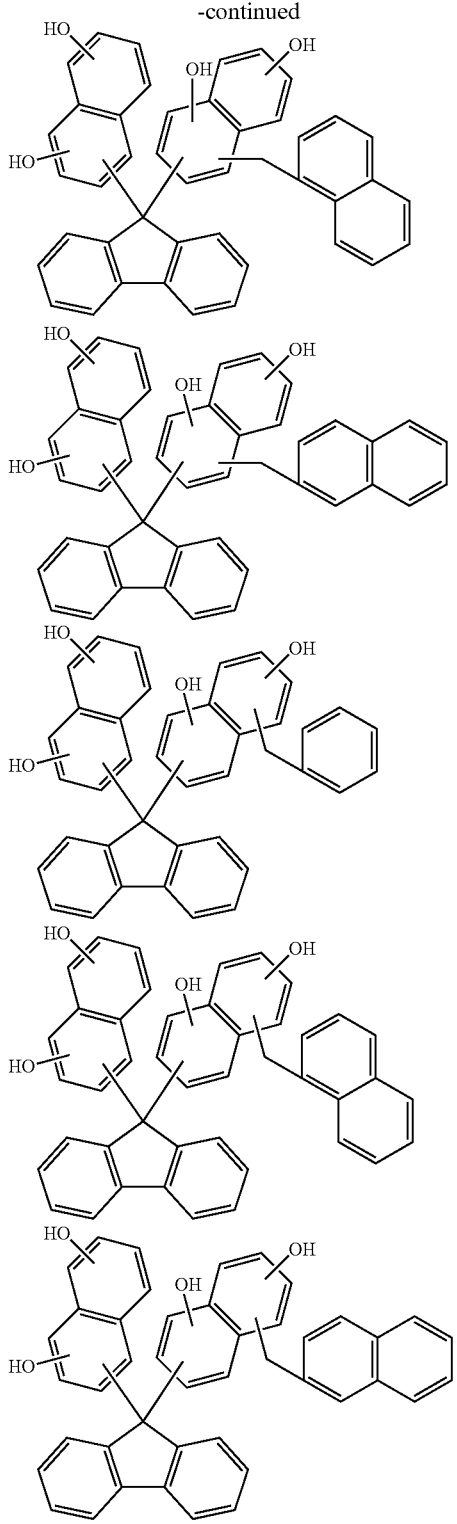

Such a compound mentioned above has a cardo structure based on a quaternary carbon and thus possesses an extremely high heat resistance.

In the case of forming an inorganic hard mask intermediate film such as a silicon oxide film, silicon nitride film or silicon oxynitride film on a resist underlayer film by CVD or the like, high temperatures exceeding 300° C. are required particularly in the case of intermediate films based on nitride films, so that the resist underlayer film is also required to possess a higher heat resistance.

Further, examples of aldehydes represented by the foregoing general formula (3) include formaldehyde, benzaldehyde, acetaldehyde, propylaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, 1-naphthaldehyde, 2-naphthaldehyde, furfural and the like. Among them, preferable are formaldehyde, benzaldehyde, 1-naphthaldehyde, 2-naphthaldehyde and the like.

Among them, in particular, formaldehyde can be used suitably. In addition, each of these aldehydes can be used solely and two or more kinds thereof can also be used in combination. An amount of the aldehydes to be used is preferably 0.2 to 5 moles or more preferably 0.5 to 2.0 moles relative to 1 mole of the compound represented by the foregoing general formula (2).

Formaldehyde can be supplied by using formaldehyde solution to be used generally. In addition, formaldehyde can also be supplied by using an arbitrary compound such as paraformaldehyde, hexamethylenetetramine and acetals such as formaldehyde dimethyl acetal as long as it exhibits the same reactivity as formaldehyde in the polycondensation reaction.

Further, the compound (C1) is obtained by condensation between a compound represented by the general formula (2) and a compound represented by the general formula (3) by an acid catalyst. Here, specific examples of the acid catalyst include an acid catalyst such as hydrochloric acid, nitric acid, sulfuric acid, formic acid, oxalic acid, acetic acid, methanesulfonic acid, camphorsulfonic acid, tosic acid and trifluoromethanesulfonic acid. An amount of these acid catalysts to be used is preferably $1 \times 10^{-5}$ to $5 \times 10^{-1}$ mole relative to 1 mole of the compound represented by the general formula (2)

As a solvent for the polycondensation reaction, for example, water, methanol, ethanol, propanol, butanol, tetrahydrofuran, dioxane, toluene, dichloromethane, dichloroethane, methylcellosolve, methoxypropyl acetate, gamma-butyrolactone, butylcellosolve or a mixture thereof can be used. These solvents are preferably in the range of 0 to 2,000 parts by mass relative to 100 parts by mass of reaction starting materials.

A reaction temperature can be appropriately determined according to reactivity of the reaction starting materials, and is usually in the range of 10° C. to 200° C.

Examples of a process of polycondensation include: a method configured to collectively charge the compound represented by the general formula (2), the compound represented by the general formula (3), and the acid catalyst, into a system; and a method configured to supply, in a dropwise manner, the compound represented by the general formula (2) and the compound represented by the general formula (3) into a system in the presence of the catalyst. After termination of the polycondensation reaction, the temperature of a reaction pot is elevated to 130 to 230° C. so as to remove unreacted fractions of the reaction starting materials, the acid catalyst, and the like which are present in the system, thereby enabling to remove volatile fractions at about 1 to 50 mmHg.

A single kind of the compound represented by the foregoing general formula (2) may be polymerized solely, and two or more kinds of the compound represented by the foregoing general formula (2) may also be used in combination for the polymerization.

A weight average molecular weight (Mw) of the compound (C1) in terms of polystyrene, which is obtained by condensation between the compound represented by the general formula (2) and the compound represented by the general formula (3) by an acid catalyst, is preferably 1,000 to 30,000 or particularly 1,500 to 20,000. A molecular weight distribution to be used is preferably in the range of 1.2 to 7.

The resist underlayer film composition of the present invention preferably includes (C) a resin containing an aromatic ring which contains such a compound (C1), thereby enabling the thus formed resist underlayer film to be excellent in filling up a step of a substrate, to have a solvent resistance and further to suppress generation of wiggling more effectively in etching a substrate, to make pattern roughness after etching favorable.

In addition, resins described in paragraphs (0028) to (0029) of Japanese Patent Laid-Open (kokai) No. 2006-227391 may be used as other resins (C) containing an aromatic ring.

Further, it is preferable that the resist underlayer film composition of the present invention includes (D) a compound containing a phenolic hydroxyl group. The compound represented by the foregoing general formula (2) is preferable as such a compound (D) containing a phenolic hydroxyl group. In addition, compounds such as phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-isopropylphenol, 4-isopropylphenol, 2-isopropylphenol, 3-isopropylphenol, 4-isopropylphenol, 2-methoxy-5-methylphenol, 2-t-butyl-5-methylphenol, pyrogallol, thymol, isothymol, 1-naphthol, 2-naphthol, 1-anthracenol, 1-pyrenol and 9-phenanthrenol can be used.

Into the resist underlayer film composition of the present invention, an acid generator (E) can be added to further promote a thermal cross-linking reaction. There are acid generators such as one generating an acid by thermal decomposition and one generating an acid by light irradiation, and any one can be added. Specifically, compositions described in paragraphs (0061) to (0085) of Japanese Patent Laid-Open (kokai) No. 2007-199653 can be added.

As a crosslinker (F) usable for the resist underlayer film composition of the present invention, compositions described in paragraphs (0055) to (0060) of Japanese Patent Laid-Open (kokai) No. 2007-199653 can be added.

Further, into the resist underlayer film composition of the present invention, a surfactant (G) can also be added to improve coatability in spin coating. Here, surfactants described in paragraphs (0142) to (0147) of Japanese Patent Laid-Open (kokai) No. 2009-269953 can be used.

Furthermore, into the resist underlayer film composition of the present invention, a basic compound can be blended to improve a storage stability. The basic compound acts as a quencher to an acid to prevent trace of the acid generated from the acid generator from proceeding with a cross-linking reaction.

Specifically, compositions described in paragraphs (0086) to (0090) of Japanese Patent Laid-Open (kokai) No. 2007-199653 can be added as such a basic composition.

In the process for forming a resist underlayer film of the present invention, the above resist underlayer film composition is coated onto a substrate to be processed by a method such as spin coating. Adopting the spin coating or the like, allows for obtainment of an excellent filling-up characteristic. After spin coating, baking thereof is conducted in order to evaporate the solvent of the composition, and to promote a cross-linking reaction therein so as to prevent mixing of the composition with a resist upper layer film, or a resist intermediate layer film. The baking is conducted at a temperature within a range between 200° C. or more and 600° C. or less, for 10 to 600 seconds or preferably for 10 to 300 seconds. The baking temperature is more preferably between 350° C. or more and 500° C. or less. In consideration of affections on device damage and wafer deformation, the upper limit of heating temperature in a wafer process of lithography is 600° C. or less or preferably 500° C. or less.

As described in SPIE Vol. 469 p. 72 (1984), especially a novolac resin generates a phenoxy radical by being heated, to activate a methylene group of the novolac bond, and thereby the methylene groups are bonded and cross-linked with each other. Since this reaction is a radical reaction, an eliminated molecule does not generate. Therefore, a composition having a high heat resistance does not cause film shrinkage due to cross-linking.

Further, in the process for forming a resist underlayer film of the present invention, the above resist underlayer film composition is coated on a substrate and the resist underlayer film composition is based in an atmosphere with an oxygen concentration of 0.1% or more and 21% or less to be cured, thereby forming a resist underlayer film.

The resist underlayer film composition of the present invention is baked in such an oxygen atmosphere, thereby enabling to obtain a fully cured resist underlayer film.

Baking atmosphere may be air, and inert gas such as $N_2$, Ar and He may be filled.

Meanwhile, a thickness of this resist underlayer film is appropriately selected, but preferable is 30 to 20,000 nm or particularly 50 to 15,000 nm. After forming the resist underlayer film, in the case of a three-layer process, a silicon-containing resist intermediate layer film and a resist upper layer film without silicon can be formed thereon in order.

The resist underlayer film composition of the present invention is extremely useful for a resist underlayer film composition for a multilayer resist process such as a silicon-containing two-layer resist process, a three-layer resist process using a silicon-containing intermediate layer film and a four-layer resist process using a silicon-containing intermediate layer film and an organic antireflection film.

A patterning process using the resist underlayer film composition of the present invention is explained below by referring to the three-layer resist process.

The patterning process of the present invention is a patterning process comprising the steps of: at least, forming a resist underlayer film on the substrate by using the resist underlayer film composition; forming a resist intermediate layer film on the resist underlayer film by using a resist intermediate layer film composition containing a silicon atom; forming a resist upper layer film on the resist intermediate layer film by using a resist upper layer film composition composed of a photoresist composition, to form a multilayer resist film; conducting exposure of a pattern circuit region of the resist upper layer film and then developing it by a developer to form a resist pattern in the resist upper layer film; etching the resist intermediate layer film by using the pattern-formed resist upper layer film as a mask; etching the resist underlayer film by using the pattern-formed resist intermediate layer film as a mask; and moreover, etching the substrate by using the pattern-formed resist underlayer film as a mask, to form a pattern on the substrate.

As mentioned above, it is preferable that etching of the resist underlayer film by using the resist intermediate layer film as a mask is performed by using an etching gas mainly comprising an oxygen gas or a hydrogen gas. It is because the silicon-containing intermediate layer film has an etching resistance to an oxygen gas or a hydrogen gas.

Further, the present invention provides a patterning process for forming a pattern on a substrate by lithography, comprising the steps of: at least, forming a resist underlayer film on the substrate by using the resist underlayer film composition; forming an inorganic hard mask intermediate film selected from a silicon oxide film, a silicon nitride film and a silicon oxynitride film on the resist underlayer film; forming a resist upper layer film on the inorganic hard mask intermediate film by using a resist upper layer film composition composed of a photoresist composition; conducting exposure of a pattern circuit region of the resist upper layer film and then developing it by a developer to form a resist pattern in the resist upper layer film; etching the inorganic hard mask intermediate film by using the obtained resist pattern as an etching mask; etching the resist underlayer film by using the obtained inorganic hard mask intermediate film pattern as an etching mask; and etching the substrate by using the obtained resist underlayer film pattern as an etching mask, to form a pattern on the substrate.

As mentioned above, in the case of forming the inorganic hard mask intermediate layer film on the resist underlayer film, a silicon oxide film, a silicon nitride film and a silicon oxynitride film (SiON film) are formed by CVD method, ALD method or the like. The forming process of the silicon nitride film is described in Japanese Patent Laid-Open (kokai) No. 2002-334869 and WO2004/066377. A film thickness of the inorganic hard mask is 5 to 200 nm or preferably 10 to 100 nm, and in particular, a SiON film which has high effects as an antireflection film is most preferably used among these inorganic hard masks. A substrate temperature in forming the SiON film is raised up to 300° C. to 500° C., so that it is necessary for the resist underlayer film to have a heat resistance to high temperature of 300° C. to 500° C. The resist underlayer film composition used in the patterning process of the present invention has a high resistance to high temperature of 300° C. to 500° C., so that the inorganic hard mask formed by CVD method or ALD method and the resist underlayer film formed by spin coating method can be used in combination.

Further, the present invention can be used suitably for a resist underlayer film of a four-layer resist process using an organic antireflection film. In this case, the present invention can provide a patterning process comprising the steps of: at least, forming a resist underlayer film on the substrate by using the resist underlayer film composition; forming an inorganic hard mask intermediate film selected from a silicon oxide film, a silicon nitride film and a silicon oxynitride film on the resist underlayer film; forming an organic antireflection film on the inorganic hard mask intermediate film; forming a resist upper layer film on the organic antireflection film by using a resist upper layer film composition composed of a photoresist composition; conducting exposure of a pattern circuit region of the resist upper layer film and then developing it by a developer to form a resist pattern in the resist upper layer film; etching the organic antireflection film and the inorganic hard mask intermediate film by using the obtained resist pattern as an etching mask; etching the resist underlayer film by using the obtained inorganic hard mask intermediate film pattern as an etching mask; and etching the substrate by using the obtained resist underlayer film pattern as an etching mask, to form a pattern on the substrate.

Although it is possible to form a photoresist film as the resist upper layer film on the resist intermediate layer film directly, it is also possible to once form an organic antireflective film (BARC) by spin coating on the resist intermediate layer film and to subsequently form a photoresist film on the organic antireflective film as mentioned above. In the case of adopting a SiON film as the resist intermediate layer film, it is enabled to restrict reflection by virtue of the two-layer antireflective films, i.e., the SiON film and BARC film, even by a liquid immersion exposure at a higher NA exceeding 1.0. Another merit of the formation of the BARC resides in obtainment of an effect to decrease footing (trailing) of a photoresist pattern compared to a photoresist pattern just above the SiON film.

As the silicon-containing resist intermediate layer film in the three-layer process, a polysilsesquioxane-based intermediate layer film is also preferably used. This makes the resist intermediate layer film to possess an effect as an antireflective film, thereby enabling to restrict reflection. Particularly, when a composition configured to contain many aromatic groups so as to possess a higher resistance against substrate-etching is used as a resist underlayer film for 193 nm exposure, a k value is rather increased to increase a substrate reflection. Nonetheless, the reflection is restricted by the resist intermediate layer film, thereby enabling to restrict the substrate reflection down to 0.5% or less. Preferably used as the resist intermediate layer film having an antireflective effect is a polysilsesquioxane, which has a pendant anthracene for exposure of 248 nm or 157 nm, or a pendant phenyl group or a pendant light-absorbing group having a silicon-silicon bond for 193 nm exposure, and which is cross-linked by an acid or a heat.

In this case, formation of the silicon-containing resist intermediate layer film by spin coating is more convenient and has a merit of cost than by a CVD method.

The resist upper layer film in the three-layer resist film may be either a positive type or negative type, and it is possible to use therefor the same one as a typically used photoresist composition. In the case of forming a single resist upper layer film by the photoresist composition, spin coating is to be preferably used similarly to the case for forming the resist underlayer film. Prebaking is to be conducted after spin coating of the photoresist composition, preferably at 60 to 180° C. for 10 to 300 seconds. Thereafter, exposure is to be conducted according to a usual manner, followed by post-exposure baking (PEB) and development, to thereby obtain a resist pattern. Although the film thickness of the resist upper layer film is not particularly limited, the film thickness is to be preferably 30 to 500 nm, particularly 50 to 400 nm.

Further, examples of light for exposure include high energy beams at wavelengths of 300 nm or shorter, specifically excimer lasers at 248 nm, 193 nm, and 157 nm, soft X-rays at 3 to 20 nm, an electron beam, X-rays, and the like.

Next, etching is to be conducted by using the obtained resist pattern as a mask. Etching of a resist intermediate layer film, particularly an inorganic hard mask, in a three-layer process is to be conducted by using the resist pattern as a mask and by adopting a flon-based gas. Next, etching of the resist underlayer film is to be conducted by using the resist intermediate film pattern, particularly the inorganic hard mask pattern, as a mask and by adopting an oxygen gas or a hydrogen gas.

The subsequent etching of a substrate to be processed can also be conducted according to a usual manner, for example, the manner that etching mainly based on a flon-based gas is conducted for a substrate made of $SiO_2$, SiN or silica-based low dielectric constant insulating film, or etching mainly based on a chlorine-based or bromine-based gas is conducted for a substrate made of p-Si, Al or W. When substrate processing is conducted by etching by a floe-based gas, the silicon-containing intermediate layer of the three-layer process is stripped simultaneously with the substrate processing. Only, in the case of etching of a substrate by a chlorine-based gas or a bromine-based gas, stripping of the silicon-containing intermediate layer is required to be separately conducted by dry etching stripping by a flon-based gas after substrate processing.

The resist underlayer film of the present invention is characterized in that the film is excellent in etching resistance in etching of a substrate to be processed mentioned above.

It is noted that examples of a substrate to be processed embrace a layer to be processed formed on a substrate. Examples of a substrate to be used are not particularly limited and include those made of materials such as Si, α-Si, p-Si, $SiO_2$, SiN, SiON, W, TiN and Al, which are different from those of layers to be processed. Examples of a layer to be processed to be used include various low-k films made of materials such as Si, $SiO_2$, SiON, SiN, p-Si, α-Si, W, W—Si, Al, Cu and Al—Si, and stopper films therefor, which can each typically form into a thickness of 50 to 10,000 nm, particularly 100 to 5,000 nm.

An example of the three-layer resist process will be specifically explained by referring to FIG. 1, as follows.

In the case of the three-layer resist process, the process is configured to form a resist underlayer film 3 on a layer to be processed 2 laminated on a substrate 1, to thereafter form a resist intermediate layer film 4 thereon, and to form a resist upper layer film 5 thereon, as shown in FIG. 1(A).

Next, as shown in FIG. 1(B), exposure is conducted for required portions 6 of the resist upper layer film, followed by PEB and development, to form a resist pattern 5a (FIG. 1(C)). The thus obtained resist pattern 5a is then used as a mask, to etch the resist intermediate layer film 4 by using a CF-based gas, to thereby form a resist intermediate layer film pattern 4a (FIG. 1(D)). After removing the resist pattern 5a, the obtained resist intermediate layer film pattern 4a is used as a mask to etch the resist underlayer film 3 by using an oxygen-plasma, to thereby form a resist underlayer film pattern 3a (FIG. 1(E)). Further, after removing the resist intermediate layer film pattern 4a, the resist underlayer film pattern 3a is used as a mask to etch the layer to be processed 2, to thereby form a pattern 2a (FIG. 1(F)).

In the case of using an inorganic hard mask intermediate film, the resist intermediate layer film 4 is the inorganic hard mask intermediate film, and in the case of arranging a BARC, a BARC layer is provided between the resist intermediate layer film 4 and the resist upper layer film 5. There is a case that etching of the BARC is to be continuously conducted prior to etching of the resist intermediate layer film 4, and it is also possible to conduct etching of the BARC only and to subsequently change an etching apparatus to conduct etching of the resist intermediate layer film 4, for example.

EXAMPLES

Hereinafter, the present invention will be explained specifically by Example and Comparative Example, but the present invention is not limited to these descriptions.

Measurement of a molecular weight is conducted by the following method.

A weight average molecular weight (Mw) and a number average molecular weight (Mn) in terms of polystyrene based on a gel permeation chromatography (GPC) were measured and dispersibility (Mw/Mn) was evaluated.

Synthesis Example 1

Synthesis of a Fullerene Derivative

Synthesis Example 1-1

Synthesis of Compound (F1)

50.0 g of nanom mix ST (mixed fullerene containing $C_{60}$ (approx. 60%), $C_{70}$ (approx. 25%) and other higher fullerenes, manufactured by Frontier Carbon Corporation), 52.3 g of t-butyl chloroacetate, 2500 g of o-xylene were stirred and mixed in a water bath under nitrogen atmosphere, and then 46.7 g of t-butoxypotassium was added, and the mixture was stirred for 16 hours. Acetic acid was added into the reaction mixture to neutralize the mixture, and then the mixture was diluted by tetrahydrofuran, and undissolved substances were filtered out. Thus obtained liquid after filtering were concentrated under reduced pressure, and then purified by silica gel column chromatograph to obtain 79.4 g of a compound (F1) as a blackish brown solid (yield: 89%). IR, $^1$H-NMR and LC-QTOF results of the synthesized compound (F1) are shown below.

(F1)

IR (D-ATR):
ν=2974, 2930, 2869, 1728, 1608, 1474, 1454, 1392, 1367, 1293, 1251, 1214, 1144 and 843 $cm^{-1}$
$^1$H-NMR (600 MHz in DMSO-d6/$CDCl_3$):
δ=0.8-2.0 (9H×n), 3.4-5.4 (1H×n)
LC-QTOF (Positive/aq.$AcONH_4$-MeCN):
m/z=1308 ($C_{90}H_{50}O_{10}$+$NH_4^+$, n=5/$C_{60}$), 1194 ($C_{84}H_{40}O_8$+$NH_4^+$, n=4/$C_{60}$), 1422 ($C_{96}H_{60}O_{12}$+$NH_4^+$/n=6/$C_{60}$), 1537 ($C_{102}H_{70}O_{14}$+$NH_4^+$, n=7/$C_{60}$), 1651 ($C_{108}H_{80}O_{16}$+$NH_4^+$, n=8/$C_{60}$), 1314 ($C_{94}H_{40}O_8$+$NH_4^+$, n=4/$C_{70}$), 1428 ($C_{100}H_{50}O_{10}$+$NH_4^+$, n=5/$C_{70}$)

Synthesis Examples 1-2 to 1-4

Synthesis of Compounds (F2) to (F4)

Compounds (F2) to (F4) shown below were obtained as a blackish brown solid in a similar manner to that of (Synthesis Example 1-1) except that each corresponding chloroacetic acid ester was used instead of t-butyl chloroacetate.

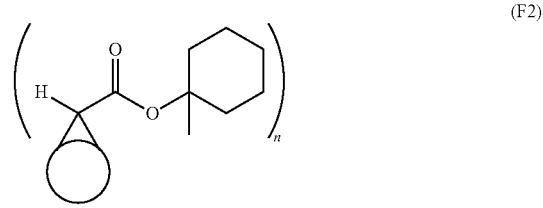

(F2)

(F3)

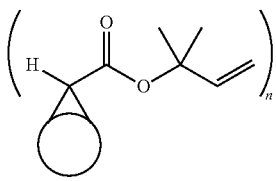

(F4)

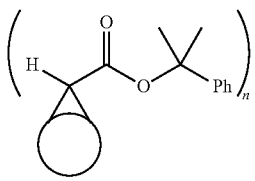

Synthesis Example 2

Synthesis of Polymer (R1)

Into a 1-L flask were added 95 g of 9,9-bis(4-hydroxy-3-methylphenyl)fluorene, 7 g of 37% aqueous formalin solution, 5 g of paratoluenesulfonic acid, 200 g of dioxane, and then they were stirred at 100° C. for 24 hours. After the reaction, the resulting mixture was dissolved in 500 mL of methyl isobutyl ketone, and then washed thoroughly by water to remove a catalyst and metallic impurities. The solvent was removed under reduced pressure, and then water and unreacted monomers were removed by reducing the pressure of the system to 2 mmHg at 150° C. to obtain polymer (R1).

Molecular weight (Mw) and dispersivity (Mw/Mn) were obtained from GPC. The results are as shown below.

Polymer (R1): Mw 9,500, Mw/Mn 3.90

Preparation of Resist Underlayer Film Compositions (UDL-1 to UDL-5 and Com. UDL-1 and Com. UDL-2)

Above-mentioned compositions (F1) to (F4) and polymer (R1), an acid generator represented by AG1, a crosslinker represented by CR1, a solvent were dissolved in a solvent containing 0.1% by mass of FC-4430 (manufactured by Sumitomo 3M Ltd.) with a ratio shown in Table 1. The resulting mixture was filtered through a 0.1 μm filter made of a fluorinated polymer, thereby preparing each resist underlayer film composition (UDL-1 to UDL-5 and Com. UDL-1 and Com. UDL-2). AG1 used as the acid generator and CR1 used as the crosslinker were shown below.

TABLE 1

| Resist Underlayer Film Composition | Fullerene Derivative (part by mass) | Polymer (part by mass) | Crossliner (part by mass) | Acid Generator (part by mass) | Solvent (part by mass) |
|---|---|---|---|---|---|
| UDL-1 | F1 (10) | R1 (10) | | | PGMEA(90)/cyclohexanone (90) |
| UDL-2 | F2 (10) | R1 (10) | | | cyclohexanone (180) |
| UDL-3 | F3 (10) | R1 (10) | | | cyclohexanone (180) |
| UDL-4 | F4 (10) | R1 (10) | | | cyclohexanone (180) |
| UDL-5 | F1 (10) | R1 (10) | CR1 (2) | AG1 (1) | PGMEA(99)/cyclohexanone (99) |
| Com. UDL-1 | — | R1 (10) | | | PGMEA(45)/cyclohexanone (45) |
| Com, UDL-2 | — | R1 (10) | CR1 (2) | AG1 (1) | PGMEA(54)/cyclohexanone (54) |

PGMEA: propylene glycol monomethyl ether acetate

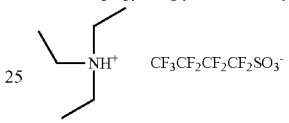

AG1

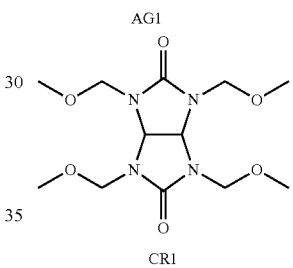

CR1

Measurement of Solvent Resistance (Examples 1 to 5, Comparative Examples 1 and 2)

Resist underlayer film compositions prepared as above (UDL-1 to UDL-5 and Com. UDL-1 and Com. UDL-2) were coated on silicon substrates, baked at a condition shown in Table 2, and then a film thickness of each was measured. A PGMEA solution was dispensed on it, allowed to stand for 30 seconds, spin-dried, baked at 100° C. for 60 seconds to evaporate PGMEA, and then a film thickness was measured. Then, a difference in film thicknesses before and after the PGMEA treatment was obtained.

TABLE 2

| No. | Resist Underlayer Film Composition | Film Thickness after Film Formation: a (Å) | Film Thickness after PGMEA Treatment: b (Å) | b/a × 100 (%) | Temperature | Atmosphere |
|---|---|---|---|---|---|---|
| Ex. 1 | UDL-1 | 2411 | 2410 | 100 | 300° C. × 60 sec | Nitrogen |
| Ex. 2 | UDL-2 | 2255 | 2254 | 100 | 300° C. × 60 sec | Nitrogen |
| Ex. 3 | UDL-3 | 2324 | 2324 | 100 | 300° C. × 60 sec | Nitrogen |
| Ex. 4 | UDL-4 | 2282 | 2279 | 100 | 300° C. × 60 sec | Nitrogen |
| Ex. 5 | UDL-5 | 2386 | 2385 | 100 | 300° C. × 60 sec | Nitrogen |
| Com. Ex. 1 | Com. UDL-1 | 2440 | 2440 | 100 | 300° C. × 60 sec | Nitrogen |
| Com. Ex. 2 | Com. UDL-2 | 2463 | 2461 | 100 | 300° C. × 60 sec | Nitrogen |

In each resist underlayer film composition of the present invention, a solvent-insoluble film was formed and film loss due to a solvent-treatment was largely suppressed, and therefore solvent resistance (resistance against a solvent) could be obtained.

Etching Test by a CF$_4$/CHF$_3$ Gas System (Examples 6 to 10 and Comparative Examples 3 and 4)

Resist underlayer films were formed in a similar manner to the above, and then an etching test was done by a CF$_4$/CHF$_3$ gas system with the following conditions.

Etching Conditions:

| | |
|---|---|
| Chamber pressure: | 40.0 Pa |
| RF power: | 1,300 W |
| CHF$_3$ gas flow rate: | 30 mL/minute |
| CF$_4$ gas flow rate: | 30 mL/minute |
| Ar gas flow rate: | 100 mL/minute |
| Time: | 60 seconds |

Film loss was evaluated by measuring film thickness before and after etching by using an etching instrument TE-8500 (manufactured by Tokyo Electron Ltd.). The results are shown in Table 3.

TABLE 3

| No. | Resist Underlayer Film Composition | Film Thickness before Etching: a' (A) | Film Thickness after Etching: b' (A) | b'/a' × 100 (%) |
|---|---|---|---|---|
| Ex. 6 | UDL-1 | 2488 | 1490 | 59.9 |
| Ex. 7 | UDL-2 | 2497 | 1490 | 59.7 |
| Ex. 8 | UDL-3 | 2498 | 1480 | 59.2 |
| Ex. 9 | UDL-4 | 2500 | 1491 | 59.6 |
| Ex. 10 | UDL-5 | 2497 | 1486 | 59.5 |
| Com. Ex. 3 | Com. UDL-1 | 2468 | 1285 | 52.1 |
| Com. Ex. 4 | Com. UDL-2 | 2484 | 1287 | 51.8 |

It was found that the etching resistance of the resist underlayer film compositions of the present invention (UDL-1 to UDL-5) was higher than that of the resist underlayer film compositions of Comparative Examples (Com. UDL-1 and Com. UDL-2).

Pattern Etching Test (Examples 11 to 15 and Comparative Examples 5 and 6)

Resist underlayer film compositions (UDL-1 to UDL-5 and Com. UDL-1 and Com. UDL-2) were each coated on a 300 mm Si wafer substrate having a Si % film with a film thickness of 200 nm, and then baked at 300° C. for 60 seconds to obtain a resist underlayer film having a film thickness of 250 nm. Here, baking of the resist underlayer film was done under nitrogen gas stream.

On it, a resist intermediate layer film composition SOG1 was coated, and then baked at 200° C. for 60 seconds to form a resist intermediate layer film having a film thickness of 35 nm. On it, an SL resist for ArF, that is a resist upper layer film composition, was coated, and then baked at 105° C. for 60 seconds to form a photoresist film having a film thickness of 100 nm. An immersion top coat composition (TC-1) was coated on the photoresist film, and then baked at 90° C. for 60 seconds to form a top coat having a film thickness of 50 nm.

As the resist intermediate layer film composition (SOG-1), 2% propylene glycol ethyl ether solution of the following polymer was prepared.

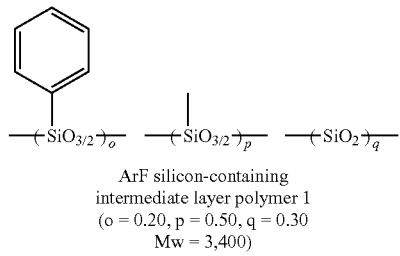

ArF silicon-containing intermediate layer polymer 1
(o = 0.20, p = 0.50, q = 0.30
Mw = 3,400)

The resist upper layer film composition (an SL resist for ArF) was prepared by dissolving a resin shown as an ArF monolayer resist polymer 1, an acid generator PAG 1, and a basic compound amine 1 in a solvent containing 0.1% by mass of FC-430 (manufactured by Sumitomo 3M Ltd.) with a ratio as shown in Table 4 followed by filtering the resulting mixture through a 0.1 µm filter made of a fluorinated resin.

TABLE 4

| No. | Polymer (parts by mass) | Acid Generator (parts by mass) | Basic Compound (parts by mass) | Solvent (parts by mass) |
|---|---|---|---|---|
| SL Resist for ArF | ArF monolayer resist polymer 1 (100) | PAG 1 (6.6) | amine 1 (0.8) | PGMEA (2,500) |

An ArF monolayer resist polymer 1, PAG 1 and amine 1 are shown below.

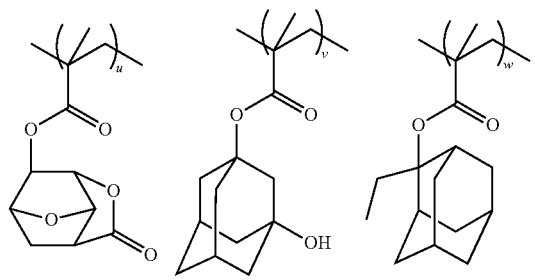

ArF monolayer resist polymer 1
(u = 0.40, v = 0.30, w = 0.30 Mw 7,800)

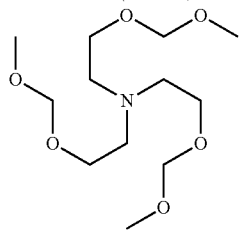

amine 1

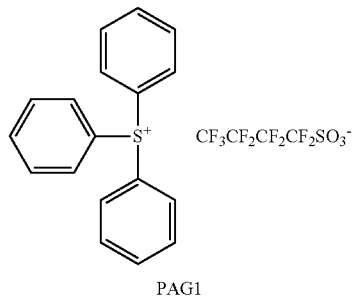

PAG1

The immersion top coat composition (TC-1) was prepared by dissolving a top coat polymer in an organic solvent with a ratio as shown in Table 5 followed by filtering the resulting mixture through a 0.1 μm filter made of a fluorinated resin.

TABLE 5

| No. | Polymer (parts by mass) | Organic solvent (parts by mass) |
| --- | --- | --- |
| TC-1 | Top coat polymer (100) | Diisoamyl ether (2,700) 2-methyl-1-butanol (270) |

The used top coat polymer is shown below.
Top-coat Polymer:
Molecular weight (Mw): 8,800
Dispersivity (Mw/Mn): 1.69

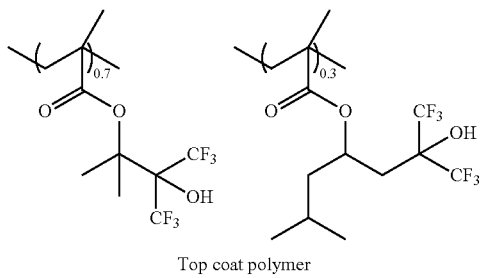

Top coat polymer

Then, it was exposed with an ArF immersion exposure instrument NSR-S610C (NA 1.30., σ 0.98/0.65, 35° dipole s-polarized light illumination, and a 6% half tone phase shift mask, manufactured by Nikon Corp.), baked (PEB) at 100° C. for 60 seconds, and then developed by a 2.38 mass % aqueous tetramethyl ammonium hydroxide (TMAH) solution for 30 seconds to obtain a 43 nm 1:1 positive line-and-space pattern.

Then, with the use of an etching instrument Telius (manufactured by Tokyo Electron Ltd.), a resist intermediate layer film was dry etched by using the resist pattern as a mask, then a resist underlayer film was etched by using the obtained resist intermediate layer film pattern as a mask, and further a SiO$_2$ film was etched by using the obtained resist underlayer film pattern as a mask. Etching conditions are as following.

Transcription conditions of the resist pattern to the resist intermediate layer film:

| | |
| --- | --- |
| Chamber pressure: | 10.0 Pa |
| RF power: | 1,500 W |
| CF$_4$ gas flow rate: | 75 sccm |
| O$_2$ gas flow rate: | 15 sccm |
| Time: | 15 seconds |

Transcription conditions of the resist intermediate layer film pattern to the resist underlayer film:

| | |
| --- | --- |
| Chamber pressure: | 2.0 Pa |
| RF power: | 500 W |
| Ar gas flow rate: | 75 sccm |
| O$_2$ gas flow rate: | 45 sccm |
| Time: | 120 seconds |

Transcription conditions of the resist underlayer film pattern to the SiO$_2$ film:

| | |
| --- | --- |
| Chamber pressure: | 2.0 Pa |
| RF power: | 2,200 W |
| C$_5$F$_{12}$ gas flow rate: | 20 sccm |
| C$_2$F$_6$ gas flow rate: | 10 sccm |
| Ar gas flow rate: | 300 sccm |
| O$_2$: | 60 sccm |
| Time: | 90 seconds |

A pattern cross-section was observed with an electron microscope S-4700 (manufactures by Hitachi, Ltd.), and pattern profile were compared. The results are shown in Tables 6.

TABLE 6

| | Resist Underlayer Film Composition | Pattern Profile after Development | Profile after Transcription Etching of Intermediate Layer | Profile after Transcription Etching of Underlayer Film | Profile after Transcription Etching of Substrate | Pattern Wiggling after Transcription Etching of Substrate |
| --- | --- | --- | --- | --- | --- | --- |
| Ex. 11 | UDL-1 | Vertical | Vertical | Vertical | Vertical | No |
| Ex. 12 | UDL-2 | Vertical | Vertical | Vertical | Vertical | No |
| Ex. 13 | UDL-3 | Vertical | Vertical | Vertical | Vertical | No |
| Ex. 14 | UDL-4 | Vertical | Vertical | Vertical | Vertical | No |
| Ex. 15 | UDL-5 | Vertical | Vertical | Vertical | Vertical | No |
| Com. Ex. 5 | Com. UDL-1 | Vertical | Vertical | Vertical | Tapered | Yes |
| Com. Ex. 6 | Com. UDL-2 | Vertical | Vertical | Vertical | Tapered | Yes |

In the resist underlayer film composition of Examples 11 to 15, in which a fullerene derivative having a carboxyl group protected by a thermally labile group of the present invention was added, a poisoning problem in forming the upper layer pattern was not caused, and furthermore, an etching resistance in etching a substrate was improved, a pattern wiggling after transcription etching of the substrate was suppressed and pattern transcription to the substrate became favorable. On the other hand, in Comparative Examples 5 and 6, a pattern wiggling after transcription etching of substrate was generated.

The present invention is not limited to the above embodiments. The above embodiments are merely illustrative, and whatever having the substantially same configurations as the technical concept recited in the claims of the present application and exhibiting the same functions and effects are embraced within the technical scope of the present invention.

What is claimed is:

1. A resist underlayer film composition of a multilayer resist film used in lithography including (A) a fullerene derivative having a carboxyl group protected by a thermally labile group, (B) an organic solvent, and (C) a resin containing an aromatic ring, wherein the fullerene derivative has n partial structures represented by formula (I):

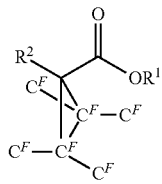

(1)

wherein:
R$^1$ represents a thermally labile group;
R$^2$ represents a hydrogen atom, a cyano group, —COOR$^3$, a linear, branched or cyclic alkyl group having 1 to 10 carbon atoms, an aryl group having 6 to 16 carbon atoms, a heteroaryl group having 4 to 16 carbon atoms or an aralkyl group having 7 to 20 carbon atoms, R$^2$ optionally containing a carbonyl group, an ether group, a ester group, a cyano group, a carboxyl group or a hydroxyl group, where R$^3$ represents a hydrogen atom, R$^1$, or a linear, branched or cyclic alkyl group having 1 to 10 carbon atoms;
C$^F$ represents a carbon atom constituting a fullerene skeleton of the fullerene derivative; and
n represents an integer of 1 to 30;

wherein the resin (C) containing an aromatic ring comprises at least a compound (C1) obtained by a polycondensation reaction between a compound represented by the following general formula (2) and a compound represented by the following general formula (3) under an acid condition,

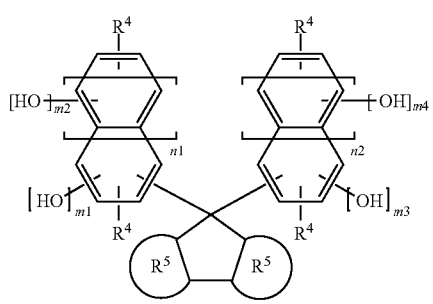

(2)

wherein:
each R$^4$ independently represents a hydrogen atom or a hydrocarbon group having 6 to 20 carbon atoms;
each R$^5$ independently represents a benzene ring or a naphthalene ring;
m1 to m4 satisfy 1≤m1+m2≤2, and 1≤m3+m4≤2; and
each n1 and n2 is 0 or 1,

A-CHO (3), wherein:
A represents:
a hydrogen atom;

a saturated or an unsaturated linear, branched, or cyclic hydrocarbon group having 1 to 20 carbon atoms; or
an aromatic hydrocarbon group having 6 to 20 carbon atoms,
A optionally containing an ether group, a nitro group, a hydroxyl group, or a chloro group.

2. The resist underlayer film composition according to claim 1, wherein the fullerene derivative has n partial structures represented by the following general formula (1a),

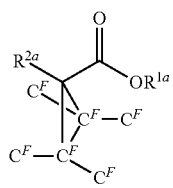

(1a)

wherein:
R$^{1a}$ represents a substituted or an unsubstituted linear or cyclic tertiary alkyl group having 4 to 30 carbon atoms, optionally containing an unsaturated bond or an aromatic ring;
R$^{2a}$ represents a hydrogen atom, a cyano group, —COOR$^{3a}$, a methyl group, an ethyl group, an acetyl group, a phenyl group, a naphthyl group, a furyl group, a benzoyl group or a naphthoyl group, R$^{3a}$ represents a hydrogen atom, R$^{1a}$, or a linear, branched or cyclic alkyl group having 1 to 10 carbon atoms;
C$^F$ represents a carbon atom constituting a fullerene skeleton of the fullerene derivative; and
n represents an integer of 1 to 30.

3. The resist underlayer film composition according to claim 1, wherein the resist underlayer film composition includes a mixture of two or more of the fullerene derivatives having a different n value from each other and the n value of a fullerene derivative having a highest presence ratio is an integer of 3 to 10.

4. The resist underlayer film composition according to claim 2, wherein the resist underlayer film composition includes a mixture of two or more of the fullerene derivatives having a different n value from each other and the n value of a fullerene derivative having a highest presence ratio is an integer of 3 to 10.

5. The resist underlayer film composition according to claim 1, further comprising at least one selected from the group consisting of:
(D) a compound containing a phenolic hydroxyl group,
(E) an acid generator,
(F) a crosslinker, and
(G) a surfactant.

6. A process for forming a resist underlayer film of a multilayer resist film used in lithography, comprising:
coating the resist underlayer film composition according to claim 1 on a substrate; and
heat treating the resist underlayer film composition at a temperature of 200° C. or more and 600° C. or less for 10 to 600 sec to be cured, thereby forming the resist underlayer film.

7. A process for forming a resist underlayer film of a multilayer resist film used in lithography, comprising:
coating the resist underlayer film composition according to claim 1 on a substrate; and baking the resist underlayer film composition in an atmosphere with an oxygen concentration of 0.1% or more and 21% or less to be cured, thereby forming the resist underlayer film.

8. A patterning process for forming a pattern on a substrate by lithography, comprising the steps of:
forming a resist underlayer film on the substrate using the resist underlayer film composition according to claim 1;
forming a resist intermediate layer film on the resist underlayer film using a resist intermediate layer film composition containing a silicon atom;
forming a resist upper layer film on the resist intermediate layer film using a resist upper layer film composition composed of a photoresist composition to form a multilayer resist film;
conducting exposure of a pattern circuit region of the resist upper layer film and then developing it with a developer to form a resist pattern in the resist upper layer film;
etching the resist intermediate layer film using the pattern-formed resist upper layer film as a mask;
etching the resist underlayer film using the pattern-formed resist intermediate layer film as a mask; and
etching the substrate using the pattern-formed resist underlayer film as a mask to form a pattern on the substrate.

9. The patterning process according to claim 8, wherein etching of the resist underlayer film using the pattern-formed resist intermediate layer film as a mask is performed using an etching gas mainly comprising an oxygen gas or a hydrogen gas.

10. A patterning process for forming a pattern on a substrate by lithography, comprising the steps of:
forming a resist underlayer film on the substrate using the resist underlayer film composition according to claim 1;
forming an inorganic hard mask intermediate film selected from a silicon oxide film, a silicon nitride film, and a silicon oxynitride film on the resist underlayer film;
forming a resist upper layer film on the inorganic hard mask intermediate film using a resist upper layer film composition composed of a photoresist composition;
conducting exposure of a pattern circuit region of the resist upper layer film and then developing it with a developer to form a resist pattern in the resist upper layer film;
etching the inorganic hard mask intermediate film using the obtained resist pattern as an etching mask;
etching the resist underlayer film using the obtained inorganic hard mask intermediate film pattern as an etching mask; and
etching the substrate using the obtained resist underlayer film pattern as an etching mask to form a pattern on the substrate.

11. A patterning process for forming a pattern on a substrate by lithography, comprising the steps of:
forming a resist underlayer film on the substrate using the resist underlayer film composition according to claim 1;
forming an inorganic hard mask intermediate film selected from a silicon oxide film, a silicon nitride film, and a silicon oxynitride film on the resist underlayer film;
forming an organic antireflection film on the inorganic hard mask intermediate film;
forming a resist upper layer film on the organic antireflection film using a resist upper layer film composition composed of a photoresist composition;
conducting exposure of a pattern circuit region of the resist upper layer film and then developing it with a developer to form a resist pattern in the resist upper layer film;
etching the organic antireflection film and the inorganic hard mask intermediate film using the obtained resist pattern as an etching mask;
etching the resist underlayer film using the obtained inorganic hard mask intermediate film pattern as an etching mask; and
etching the substrate using the obtained resist underlayer film pattern as an etching mask to form a pattern on the substrate.

12. The patterning process according to claim 10, wherein the inorganic hard mask intermediate film is formed by a CVD method or an ALD method.

13. The patterning process according to claim 11, wherein the inorganic hard mask intermediate film is formed by a CVD method or an ALD method.

* * * * *